(12) United States Patent
Iglesias

(10) Patent No.: US 10,159,659 B2
(45) Date of Patent: Dec. 25, 2018

(54) PREDICTING RESPONSE TO CANCER THERAPY

(71) Applicant: BIONOMICS LIMITED, Thebarton (AU)

(72) Inventor: Jose Iglesias, Oakville (CA)

(73) Assignee: BIONOMICS LIMITED, Thebarton, South Australia (AU)

( * ) Notice: Subject to any disclaimer, the term of this patent is extended or adjusted under 35 U.S.C. 154(b) by 0 days.

(21) Appl. No.: 15/322,647

(22) PCT Filed: Mar. 18, 2015

(86) PCT No.: PCT/AU2015/000157
§ 371 (c)(1),
(2) Date: Dec. 28, 2016

(87) PCT Pub. No.: WO2016/000012
PCT Pub. Date: Jan. 7, 2016

(65) Prior Publication Data
US 2017/0135980 A1 May 18, 2017

(30) Foreign Application Priority Data

Jul. 2, 2014 (AU) ............................... 2014902535

(51) Int. Cl.
*A61K 31/34* (2006.01)
*A61K 31/343* (2006.01)
*C12Q 1/48* (2006.01)
*A61K 31/439* (2006.01)

(52) U.S. Cl.
CPC .......... *A61K 31/343* (2013.01); *A61K 31/439* (2013.01); *C12Q 1/485* (2013.01); *G01N 2333/912* (2013.01); *G01N 2800/52* (2013.01)

(58) Field of Classification Search
CPC .... A61K 31/343; A61K 31/439; C12Q 1/485; G01N 2333/912; G01N 2800/52
USPC ................. 514/418, 445, 447, 470
See application file for complete search history.

(56) References Cited

U.S. PATENT DOCUMENTS

| 8,680,135 B2 * | 3/2014 | Chaplin | C07D 209/12 514/418 |
| 8,716,335 B2 * | 5/2014 | Chaplin | C07D 209/12 514/469 |
| 9,006,284 B2 * | 4/2015 | Kremmidiotis | A61K 31/09 514/469 |

FOREIGN PATENT DOCUMENTS

| WO | WO 2011/022772 A1 | 3/2011 |
| WO | WO 2012/009288 A2 | 1/2012 |

OTHER PUBLICATIONS

Ellis et al., "Vascular Disruption in Combination with mTOR Inhibition in Renal Cell Carcinoma", 2012, Molecular Cancer Therapeutics, 11(2), pp. 383-392. (Year: 2012).*
Bionomics Limited, "BNC105 Phase II Renal Cancer Trial Results," ASX [Australian Stock Exchange] Announcement, Mar. 19, 2014.
J. Sarantopoulos et al., "A Phase I/II Trial of BNC105P with Everolimus in Metastatic Renal Cell Carcinoma (mRCC) Patients," Abstract ID 4563, ASCO (2013).
S. von Roemeling et al., "Preclinical Evaluation of the mTOR Inhibitor, Temsirolimus, in Combination with the Epothilone B Analog, Ixabepilone in Renal Cell Carcinoma," American Journal of Cancer Research, vol. 3, No. 4, pp. 390-401 (2013).
Extended European Search Report for European Patent Application No. 15815134.0, dated Jan. 29, 2018 (7 pages).
Fuhrman, et al., "Prognostic significance of morphologic parameters in renal cell carcinoma," 1982, Am J Surg Pathol, 6(7), pp. 655-653.
Maroto, et al., "Molecular Biomarkers in Advanced Renal Cell Carcinoma," 2014, Clin Cancer Res, 20(8), pp. 2060-2071.
Vasudev, et al., "Renal cancer biomarkers: the promise of personalized care," 2012, BMC Medicine, 10(112), pp. 1-10.

* cited by examiner

*Primary Examiner* — My-Chau T. Tran
(74) *Attorney, Agent, or Firm* — Finnegan, Henderson, Farabow, Garrett & Dunner, LLP

(57) ABSTRACT

The present invention relates to cancer markers that are predictive for cancer patent response to treatment with an m TOR inhibitor and a vascular disrupting agent. The present invention further relates to methods of treating a cancer patient subpopulation with a combination of an m TOR inhibitor and a vascular disrupting agent.

14 Claims, 5 Drawing Sheets

PREDICTING RESPONSE TO CANCER THERAPY

CROSS-REFERENCE TO RELATED APPLICATIONS

This application is a national phase application of International Application No. PCT/AU2015/000157, filed Mar. 18, 2015, and claims the priority of Australian Application No. 2014902535, filed Jul. 2, 2014, the content of both of which is incorporated herein by reference.

FIELD

The present invention relates to cancer markers that are predictive for cancer patent response to treatment with an mTOR inhibitor and a vascular disrupting agent. The present invention further relates to methods of treating a cancer patient subpopulation with a combination of an mTOR inhibitor and a vascular disrupting agent.

BACKGROUND

Renal cancer accounts for more than 100,000 deaths across the world per annum. Approximately 90-95% of renal cancers arise in the renal parenchyma and are termed renal cell carcinomas. The incidence of renal cell carcinoma has been steadily rising over the past 20 years in many countries and this is thought to be only partially explained by the increased rate of incidental diagnosis (Vasudev et al., 2012)

Following surgical resection, a significant proportion of renal cancer patients will experience recurrence or present with metastatic disease at distant sites. The availability of agents directly targeting tumorigenic and angiogenic pathways has improved the outcomes of patients with advanced renal cell carcinoma (Maroto and Rini, 2014). Currently available U.S. Food and Drug Administration-approved first line targeted agents include sunitinib, pazopanib, temsirolimus, and bevacizumab (with interferon), while axitinib, everolimus, and sorafenib are most extensively used following progression as second- or third line therapy. However, all patients eventually become resistant and a substantial percentage experience immediate disease progression with first line targeted therapy. In addition, patients have variable clinical benefit and/or tolerance to different agents. Hence, the choice of therapy for an individual patient remains empiric at present.

Attempts to augment the activity of these agents by combining them together or with chemotherapy or immunotherapy have not yet proven to improve outcomes and treatment of metastatic renal cell carcinoma remains a challenge for clinicians. Thus, while current therapy has improved outcomes modestly, there remains a need to identify prognostic and predictive biomarkers that can be used to optimise treatment selection.

SUMMARY

The present inventors have identified biomarkers which delineate renal cancer patients who have an increased likelihood of responding to treatment with an mTOR inhibitor and a vascular disrupting agent when compared to treatment with an mTOR inhibitor alone.

Accordingly, in a first aspect there is provided a method for predicting a response to treatment with an mTOR inhibitor and a vascular disrupting agent in a renal cancer patient, the method comprising identifying a renal cancer patient having one or more biological markers selected from Fuhrman tumor grade of 2 or greater, presence of liver metastases, and/or prior nephrectomy, wherein a Fuhrman tumor grade of 2 or greater, the presence of liver metastases, and/or a prior nephrectomy in a patient is indicative that the patient will respond to treatment with an mTOR inhibitor and a vascular disrupting agent when compared to treatment with an mTOR inhibitor alone.

In one embodiment, the method further comprises administering an mTOR inhibitor and a vascular disrupting agent to the patient.

In a second aspect there is provided a method of treating renal cancer in a patient, the method comprising performing the method of the first aspect and treating a patient having one or more biological markers selected from Fuhrman tumor grade of 2 or greater, presence of liver metastases, and/or prior nephrectomy with an mTOR inhibitor and a vascular disrupting agent.

In one embodiment, the response to treatment is an increase in progression free survival compared to a patient who has not been administered the mTOR inhibitor and the vascular disrupting agent. In one particular embodiment, the increase in progression free survival is at least 10 days, at least 15 days, at least 20 days, at least 30 days, at least 40 days, or at least 50 days.

In a third aspect there is provided a method of treating renal cancer in a patient, the method comprising identifying a patient having a Fuhrman tumor grade of 2 or greater, the presence of liver metastases, and/or a prior nephrectomy and administering an mTOR inhibitor and a vascular disrupting agent to the patient.

In a fourth aspect there is provided a method of treating renal cancer in a patient, the method comprising administering an mTOR inhibitor and a vascular disrupting agent to the patient, wherein the patient has a Fuhrman tumor grade of 2 or greater, the presence of liver metastases, and/or a prior nephrectomy.

In a fifth aspect there is provided a method of selecting a renal cancer patient for treatment with an mTOR inhibitor and a vascular disrupting agent, the method comprising performing the method of the invention of predicting a response to treatment with an mTOR inhibitor and a vascular disrupting agent in a renal cancer patient, and selecting a patient having a Fuhrman tumor grade of 2 or greater, the presence of liver metastases, and/or a prior nephrectomy for treatment with an mTOR inhibitor and a vascular disrupting agent.

While the skilled person will be able to select any known suitable vascular disrupting agent, in one embodiment, the vascular disrupting agent is a tubulin polymerisation inhibitor.

In one particular embodiment, the tubulin polymerisation inhibitor is selected from ABT-751, MPC-6827, AEZS-112, CYT997, MN-029, EPC2407, ZIO-301, vinflunine, vinblastine, vincristine, CA4, Oxi4503, AVE8062, eribulin mesylate, dolastatin, tasidotin, 2-methoxyestradiol, E7974 and/or NPI-2358.

In one embodiment, the tubulin polymerisation inhibitor is a compound of formula (I) or a salt, solvate or prodrug thereof $$\text{(I)}$$

[Structure of Formula (I): a bicyclic indole-like core with substituents $R^{1A}$, $R^{1B}$, $R^{1C}$, $R^{1D}$ on one ring, linker L to a phenyl ring bearing $R^{2A}$, $R^{2B}$, $R^{2C}$, $R^{2D}$, $R^{2E}$, and X-Q on the heterocyclic ring]

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$—$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted acylamino, optionally substituted oxyacyl, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR"NR'", where each R'" independently represents H, optionally substituted alkyl, optionally substituted alkenyl, optionally substituted alkynyl, optionally substituted aryl and optionally substituted heteroaryl.

In another embodiment, the tubulin polymerisation inhibitor is a compound of formula (Ia) or a salt, solvate or prodrug thereof $$\text{(Ia)}$$

[Structure of Formula (Ia): trimethoxyphenyl group ($CH_3O$, $OCH_3$, $OCH_3$) with $R^{2E}$ and $R^{2A}$ substituents, connected via a carbonyl (C=O) linker to an indole-type bicyclic core bearing $R^{1A}$, $R^{1B}$, $R^{1C}$, $R^{1D}$ and an X-Q position]

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or R1A and R1B together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

$R^{2A}$ and $R^{2E}$ independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

In yet another embodiment, the tubulin polymerisation inhibitor is a compound of formula (Ib) or a salt, solvate or prodrug thereof

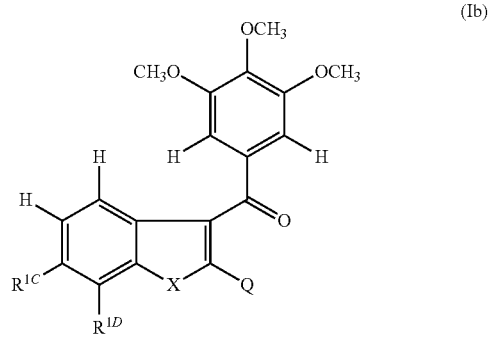

(Ib)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1C}$ represents $C_{1-3}$ alkoxy;

$R^{1D}$ represents hydroxy or amino;

Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

In yet another embodiment, the tubulin polymerisation inhibitor is a compound of formula (II) or a salt, solvate or prodrug thereof

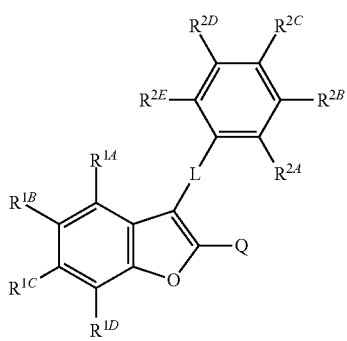

(II)

wherein;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$—$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR"NR'", where each R'" independently represents H, optionally substituted alkyl, optionally substituted alkenyl, optionally substituted alkynyl, optionally substituted aryl and optionally substituted heteroaryl.

In one embodiment, $R^{1C}$ is $C_{1-3}$ alkoxy, $R^{1D}$ is hydroxyl and Q is optionally substituted $C_{1-3}$ alkyl.

In yet another embodiment, the tubulin polymerisation inhibitor is a compound of formula (III) or a salt, solvate or prodrug thereof

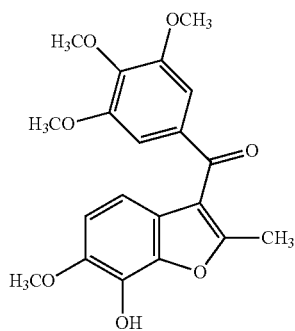 [SMILES: COc1cc(C(=O)c2c(C)oc3c(O)c(OC)ccc23)cc(OC)c1OC]

In one particular embodiment, the tubulin polymerisation inhibitor is selected from 2-methyl-7-hydroxy-3-(3,4,5-trimethoxybenzoyl)-6-methoxybenzofuran (BNC105) and disodium [6-methoxy-2-methyl-3-(3,4,5-trimethoxybenzoyl)-1-benzofuran-7-yl] phosphate (BNC105P).

In one embodiment of the methods of the invention, the mTOR inhibitor is selected from BEZ235 (NVP-BEZ235), deforolimus (AP 23573, MK-8669), PI-103, rapamycin (Sirolimus, Rapamune), temsirolimus (Toricel, CCI-779), everolimus (Afinitor, RAD001, Certican), ABT 578, SAR 543 and AP 23841.

In one particular embodiment, the tubulin polymerisation inhibitor is disodium [6-methoxy-2-methyl-3-(3,4,5-trimethoxybenzoyl)-1-benzofuran-7-yl] phosphate (BNC105P) and the mTOR inhibitor is everolimus (Afinitor, RAD001, Certican).

While the skilled person will readily be able to determine suitable doses of the mTOR inhibitor and the vascular disrupting agent, in one embodiment, everolimus is administered at a dosage of about 5 to about 15 mg.

In yet another embodiment, everolimus is administered at a dosage of about 10 mg.

In another embodiment, BNC105P is administered at a dosage of about 8 mg/m$^2$ to about 16 mg/m$^2$. In one particular embodiment, BNC105P is administered at a dosage of 16 mg/m$^2$.

The person skilled in the art will be able to determine a suitable timing of administration of the mTOR inhibitor and the vascular disrupting agent. In one embodiment, the tubulin polymerisation inhibitor and/or the vascular disrupting agent is administered three times a day, twice a day, daily, every other day, or weekly. In addition the administration may be two or more administrations of the mTOR inhibitor and/or the vascular disrupting agent. In one embodiment, the mTOR inhibitor and/or the vascular disrupting agent may be administered as a single dose, or as multiple doses (i.e. two or more doses) spread over a greater time period such as one, two or three months apart.

In one embodiment, everolimus is administered daily to the patient.

In another embodiment, BNC105P is administered to the patient in weekly doses. In one particular embodiment, everolimus is administered daily to the patient, and BNC105P is administered to the patient after about 5, 6, 7, 8 or 9 days of everolimus administration and again at about 13, 14, 15, 16, or 17 days of everolimus administration.

In some embodiments, the skilled person will be able to determine whether a renal cancer patient has one or more biomarkers selected from Fuhrman tumor grade of 2 or greater, presence of liver metastases, and/or prior nephrectomy by reference to the patient's medical history. Thus, in one embodiment, patient records are used to identify a patient having one or more biological markers selected from Fuhrman tumor grade of 2 or greater, presence of liver metastases, and/or prior nephrectomy.

The skilled person will appreciate however, that a suitable medical imaging technique, for example, such as positron emission tomography (PET)/computer tomography (CT) scans or magnetic resonance imaging (MRI), may be used to identify a renal cancer patient having liver metastases.

Additionally, in light of the present specification, the skilled person will readily be able to perform a microscopic examination, such as hematoxylin and eosin staining, in order to determine Fuhrman Tumor Grade of a patient if required.

In one embodiment, the renal cancer patient is a renal cell carcinoma patient. In one particular embodiment, the renal cell carcinoma is clear cell renal carcinoma.

In another embodiment, the renal cell carcinoma is papillary renal cell carcinoma.

As understood in the art, a combination therapy may involve the administration of multiple pharmaceutical agents separately for the treatment of a disease, or alternatively, may involve the administration of multiple drugs as a combination formulation, i.e., a formulation containing multiple pharmaceutical active ingredients. In addition, where the drugs in a combination therapy are provided as separate formulations, the drugs may be administered concurrently or sequentially.

In one embodiment of the second to fifth aspects, the mTOR inhibitor and the vascular disrupting agent are administered separately.

In another embodiment, the mTOR inhibitor is administered prior to and/or concurrently with the vascular disrupting agent.

In yet another embodiment, the mTOR inhibitor and the vascular disrupting agent are administered sequentially.

In one particular embodiment, the patient is administered the mTOR inhibitor and then subsequently administered the vascular disrupting agent.

In another embodiment, the mTOR inhibitor and the vascular disruption agent are administered as a combination formulation.

In yet another embodiment, the method comprises administering a further therapeutic agent and/or tumor irradiation to the patient.

In one embodiment, the further therapeutic agent is selected from a chemotherapeutic, an antibody and/or an immunotherapeutic.

In one embodiment, the therapeutic agent is selected from a tyrosine kinase inhibitor and/or a VEGF inhibitor.

In a sixth aspect there is provided an mTOR inhibitor and a vascular disrupting agent for use in the treatment of renal cancer in a patient having a Fuhrman tumor grade of 2 or greater, the presence of liver metastases, and/or a prior nephrectomy.

In one embodiment, the mTOR inhibitor and the vascular disrupting agent are administered separately.

In another embodiment, the mTOR inhibitor is administered prior to and/or concurrently with the vascular disrupting agent.

In yet another embodiment, the mTOR inhibitor and the vascular disrupting agent are administered as a combination formulation.

In a seventh aspect there is provided a vascular disrupting agent for use in the treatment of renal cancer in a patient having a Fuhrman tumor grade of 2 or greater, the presence of liver metastases, and/or a prior nephrectomy, wherein the patient is already being treated with an mTOR inhibitor.

In an eighth aspect there is provided use of an mTOR inhibitor and a vascular disrupting agent in the manufacture of a medicament for the treatment of renal cancer in a patient, wherein the patient has a Fuhrman tumor grade of 2 or greater, the presence of liver metastases, and/or a prior nephrectomy.

In a ninth aspect, there is provided use of a vascular disrupting agent in the manufacture of a medicament for the treatment of renal cancer in a patient, wherein the patient has a Fuhrman tumor grade of 2 or greater, the presence of liver metastases, and/or a prior nephrectomy, wherein the patient is already being treated with an mTOR inhibitor.

In a tenth aspect there is provided use of the method of predicting a response to treatment with an mTOR inhibitor and a vascular disrupting agent in a renal cancer patient of the invention to identify a renal cancer patient having an increased likelihood of responding to treatment with an mTOR inhibitor and a vascular disrupting agent compared to treatment with an mTOR inhibitor alone.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

DETAILED DESCRIPTION

General Techniques and Definitions

Figure 1:
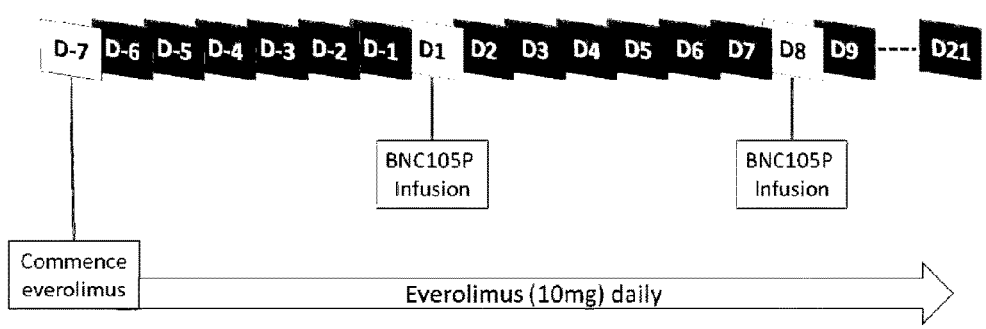
FIG. 1. Dosing schedule for administration of Afinitor (everolimus) and BNC105P.

Unless specifically defined otherwise, all technical and scientific terms used herein shall be taken to have the same meaning as commonly understood by one of ordinary skill in the art (e.g., in molecular genetics, biochemistry, and immunology).

Unless otherwise indicated, the molecular genetics, biochemistry, and immunological techniques utilized in the present invention are standard procedures, well known to those skilled in the art. Such techniques are described and explained throughout the literature in sources such as, J, Perbal, A Practical Guide to Molecular Cloning, John Wiley and Sons (1984), J. Sambrook and Russell., Molecular Cloning: A Laboratory Manual, 3$^{rd}$ edn, Cold Spring Harbour Laboratory Press (2001), R. Scopes, Protein Purification—Principals and Practice, 3$^{rd}$ edn, Springer (1994), T. A. Brown (editor), Essential Molecular Biology: A Practical Approach, Volumes 1 and 2, IRL Press (1991), D.M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J.E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10% of the designated value.

As used herein, the terms "treating", "treat" or "treatment" include administering an mTOR inhibitor and a vascular disrupting agent to a patient in an amount sufficient to prevent or delay disease progression and/or to increase the duration of progression free survival as compared to a patient who has not been administered the mTOR inhibitor and the vascular disrupting agent.

As used herein, the terms "response", "responding", "response to treatment" or "responding to treatment" refer to a patient having a reduction in one or more symptoms or signs of disease and/or a delay or prevention of disease progression, and/or a longer period of disease free progression during and/or following treatment with a combination of an mTOR inhibitor and a vascular disrupting agent when compared to a patient that has not been treated with the combination of the mTOR inhibitor and the vascular disrupting agent.

"Administering" as used herein is to be construed broadly and includes administering a composition or therapeutic agent as described herein to a subject or patient as well as providing the composition or therapeutic agent to a cell, such as, for example, by the provision of a prodrug to a patient.

Biomarkers Predictive of Patent Response to Treatment

The present inventors have determined that renal cancer patients having one or more biomarkers selected from Fuhrman Tumor Grade 2, liver metastases and/or prior nephrectomy have an increased likelihood of exhibiting a response to treatment with a combination of an mTOR inhibitor and a vascular disrupting agent when compared to treatment with an mTOR inhibitor alone.

Furhman Tumor Grade

The grading scheme of renal cell carcinoma is based on the microscopic morphology of a neoplasm with hematoxylin and eosin (H&E) staining. The most popular and widely used system for grading renal cell carcinoma is a nuclear grading system described by Fuhrman et al. in 1982. This grading system categorizes renal cell carcinoma (RCC) with grades 1, 2, 3, and 4 based on nuclear characteristics and represents one of the most significant prognostic variables in patients with all stages of renal cell carcinoma (RCC).

Grade 1: Using the 10x objective, the nuclei of the tumor cells are small (<10 μm), hyperchromatic, and round (resembling mature lymphocytes), with no visible nucleoli and little detail in the chromatin.

Grade 2: Using the 10× objective, the nuclei of the tumor cells are slightly larger (15 μm) with finely granular "open" chromatin but small, inconspicuous nucleoli. The nucleoli are often present, and many appear as small chromocenters at 10× objective, with confirmation of their nature at higher power, but this does not count.

Grade 3: Using the 10× objective, the nuclei of the tumor cells are larger (20 μm in size) and may be oval in shape, with coarsely granular chromatin. The nucleoli are easily unequivocally recognizable.

Grade 4: The nuclei are pleomorphic with open chromatin or hyperchromatic and single or multiple macronucleoli.

Liver Metastases and Nephrectomy

The metastatic stage of the renal cell carcinoma occurs when the disease invades and spreads to other organs. It is most likely to spread to neighbouring lymph nodes, the lungs, the liver, the bones, or the brain. About 70% of patients with renal cell carcinoma develop metastases during the course of their disease, and 5 year survival for patients with metastatic renal cell carcinoma is between 5-15%, though it is much improved if metastatectomy and nephrectomy to remove all visible disease is performed. Symptoms of metastatic renal cell carcinoma are often mistaken for other, less severe illness, and include: for bone metastases, pain, stiffness, bruit, and pathologic fracture; for liver metastases, abdominal pain, jaundice, elevations in AST and ALT, and vomiting, for lung metastases, cough, dyspnea, and abnormal chest radiograph. Medical imaging methods such as PET/CT scans and MRI are typically used for the identification of liver metastases.

Nephrectomy in the setting of metastatic renal cell carcinoma, commonly called cytoreductive nephrectomy, is often advocated as part of a multimodality treatment approach. Radical nephrectomy is the removal of the entire affected kidney including Gerota's fascia, the adrenal gland which is on the same side as the affected kidney, and the regional lymph nodes, all at the same time. This technique is most often used when there is a large tumour present in only one kidney.

Nephron-sparing partial nephrectomy is used when the tumor is small (less than 4 cm in diameter) or when the patient has other medical concerns such as diabetes or hypertension. The partial nephrectomy involves the removal of the affected tissue only, sparing the rest of the kidney, Gerota's fascia and the regional lymph nodes. This allows for more renal preservation as compared to the radical nephrectomy, and this can have positive long term health benefits.

Laparoscopic nephrectomy uses laparoscopic surgery, with minimally invasive surgical techniques. Commonly referred to as key hole surgery, this surgery does not have the large incisions seen in a classically performed radical or partial nephrectomy, but still successfully removes either all or part of the kidney. Laparoscopic surgery is associated with shorter stays in the hospital and quicker recovery time but there are still risks associated with the surgical procedure.

Typically, prior to treating a patient with a combination of an mTOR inhibitor and a vascular disrupting agent, the presence of liver metastases and/or prior nephrectomy is determined from a patient's medical history. In some embodiments, however, a suitable medical imaging technique, for example PET/CT scan or MRI, may be utilised in order to detect liver metastases in a renal cell cancer patient.

mTOR Inhibitors

The molecular target of rapamycin (mTOR serine/threonine kinase), also known as the mammalian target of rapamycin, mTOR, or FK506-binding protein 12-rapamycin-associated protein 1 (FRAP1), is a serine/threonine protein kinase that regulates cell growth, cell proliferation, cell motility, cell survival, protein synthesis, and transcription. MTOR belongs to the phosphatidylinositol 3-kinase-related kinase protein family. PI3K/Akt-dependent phosphorylation signals through tuberin, the protein product of the TSC1/TSC2 complex, leading to mTOR activation. mTOR subsequently phosphorylates downstream targets, causing initiation of protein translation. Accordingly, any agent that inhibits the activation of mTOR, causing down-regulation of its downstream targets, is encompassed by the meaning of "mTOR inhibitor" as used herein.

Examples of mTOR inhibitors suitable for use in the present invention include BEZ235 (NVP-BEZ235), deforolimus (AP 23573, MK-8669), PI-103, rapamycin (Sirolimus, Rapamune), temsirolimus (Toricel, CCI-779), everolimus (Afinitor, RAD001, Certican), ABT 578, SAR 543 and AP 23841. In one particular embodiment, the mTOR inhibitor is everolimus (Afinitor).

Vascular Disrupting Agents

Endothelial cells are highly dependent on the tubulin cytoskeleton for their motility, invasion, attachment, alignment and proliferation. Vascular disrupting agents (VDAs) target endothelial cells and pericytes of the already established tumor vasculature. Most VDAs induce changes in endothelial cell shape by disruption of the cytoskeleton and cell-to-cell junctions. This results in increased permeability to proteins and an increased interstitial fluid pressure, which might be sufficient to reduce vessel diameter. Plasma leakage also leads to increased blood viscosity resulting in decreased blood flow and rouleaux formation.

Another factor contributing to the vascular shutdown is the activation of platelets through contact with basement membrane components, which are exposed. All together this cascade of events results in vascular shutdown more selectively in tumor endothelium than normal endothelium. As stated previously, it is suggested that the inhibition of blood flow and the subsequent compromised supply of oxygen and nutrients will induce necrosis of many tumor cells downstream.

Vascular disrupting agents have been divided into two types, small molecule and ligand directed VDAs. Small molecule VDAs are in a more advanced stage of clinical development. Small molecule VDAs are either tubulin-binding agents or flavonoids. In one mechanism of action, tubulin-binding agents work by acting at the colchicine-binding site of the β-subunit of endothelial cell tubulin, resulting in depolymerization of microtubules and disorganization of actin and tubulin (e.g. CA4 (combretastatin)).

Disruption of the endothelial cytoskeleton results in cell morphology changes leading to reduction or cessation of blood flow. Tumor-related endothelial cells are much more sensitive to the activity of tubulin-binding agents than normal endothelial cells. ASA404 is a small-molecule flavonoid VDA with activity involving inhibition of pathways that up regulate the nuclear transcription factor NficB and production of TNF-α and other cytokines.

In one embodiment, the vascular disrupting agent is a Tubulin Polymerization Inhibitor (TPI). As used herein the term "tubulin polymerisation inhibitor" refers to any and all compounds or molecules which directly interact with tubulin and inhibit tubulin polymerisation and as a consequence interferes with the physiological function of microtubules. Tubulin polymerisation inhibitors (TPIs) are also referred to as microtubule "destabilizing" agents. Such compounds should be contrasted with tubulin interacting compounds like taxanes and epothilones which stabilise tubulin polymers and inhibit tubulin depolymerisation (i.e., microtubule stabilising agents).

Microtubules are filamentous polymers that are key components of the cell cytoskeleton. They are dynamic structures fluctuating between states of polymerisation and depolymerisation. This property enables microtubules to modulate cell shape, adhesion, migration and proliferation. TPIs interfere with microtubule integrity, leading to cytoskeletal changes of the endothelial cells that line the blood vessels of the tumour. As a result, these usually flat cells become more rounded, and lose their cell to cell contact. These events lead to narrowing of tumour blood vessels and ultimately occlusion of blood flow through the vessels. TPIs directly disrupt microtubule polymerisation processes and consequently have the ability to effect cell shape changes and inhibit cell proliferation. These properties are central to the use of TPIs as therapeutics for the treatment of cancer and in the method of the present invention.

TPIs may also be classified based on their specific tubulin binding site. Binding of vinca alkaloids to tubulin defines a site that mediates the tubulin destabilization activity seen with these compounds. The "vinca" site has been shown to directly bind a number of compounds that effect destabilization of tubulin. Examples of TPI's that bind to the vinca site include vinflunine, vinblastine, vincristine, vinorelbine, dolastatin, tasidotin and E7974.

Colchicine binding to tubulin defines an independent binding site that like in the case of the "vinca" site causes destabilization of tubulin. Although TPI's binding to the "vinca" sites have been successful as anti-cancer chemotherapeutics, "colchicine" site binders have been in comparison neglected, possibly due to the lack of therapeutic margins offered by colchicine. However, more recently a number of "colchicine" site binding agents have been described that have the ability to cause disruption of blood vessels within solid tumors. Many of the "colchicine" site binding agents are based on natural products such as combretastatins (CA4P, OXi-4503, AVE-8062), colchicines (ZD6126) and phenylahistin (NPI-2358) while others are small molecules which bind to the colchicine site (ABT-751, MPC-6827, AEZS-112, CYT-997, MN-029, EPC2407, ZIO-301, 2ME2, ZD6126 and NPI-2358).

TPI compounds are important in the treatment of cancers primarily as a result of their capacity to selectively shut down blood flow through a tumour. Targeting tubulin polymerisation inhibition has been a very well validated anti-cancer approach through the development and now extensive clinical use of chemotherapeutic TPIs.

Examples of TPIs suitable for use in the present invention include ABT-751 (E7010, Abbott), MPC-6827 (AzixaTM, Myriad Pharmaceuticals), AEZS-112 (ZEN-012, Eterna Zentaris), CYT997 (Cytopia), MN-029 (Denibulin, MediciNova/Angiogene), EPC2407 (EpiCept), ZIO-301 (Indibulin, Ziopharm Oncology), Vinflunine (Javlor, Pierre Fabre Medicament) as well as other vinca alkaloids (e.g., vinblastin, vincristine, and vinorelbine), combretastatins (CA4 (Zybrestat™, OXiGENE), Oxi4503 (OXiGENE), and AVE8062 (AC7700, Sanofi Aventis)), Eribulin Mesylate (E7389, Eisai), Dolastatin 10 (NCI), Tasidotin (synthadotin, Genzyme), 2-methoxyestradiol (2ME2 or Panzem®, EntreMed), E7974 (Eisai), and NPI-2358 (Nereus Pharmaceuticals). Examples of TPI structures are provided in Table 1.

TABLE 1

Examples of TPI structures

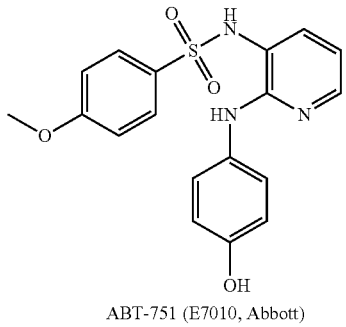 [SMILES: COc1ccc(S(=O)(=O)Nc2cccnc2Nc2ccc(O)cc2)cc1]

ABT-751 (E7010, Abbott)

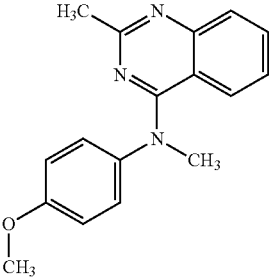

MPC-6827 (Azixa™, Myriad Pharmaceuticals)

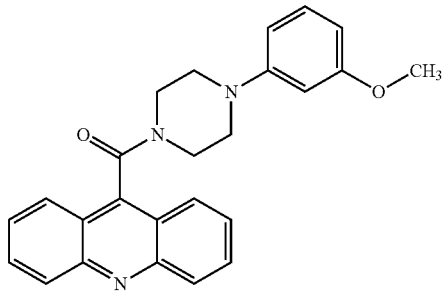

AEZS-112 (ZEN-012, Eterna Zentaris)

TABLE 1-continued
Examples of TPI structures
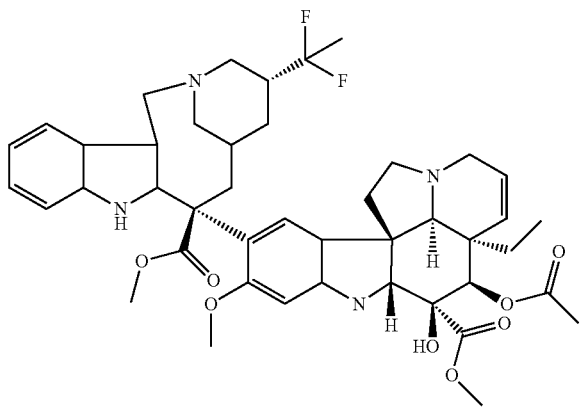
Vinflunine
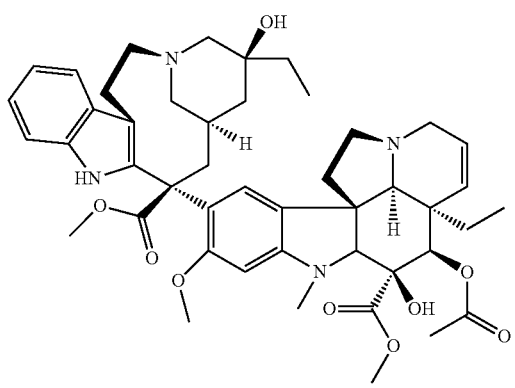
Vinblastin
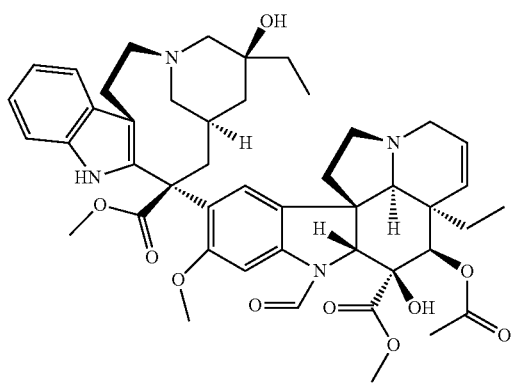
Vincristine TABLE 1-continued
Examples of TPI structures
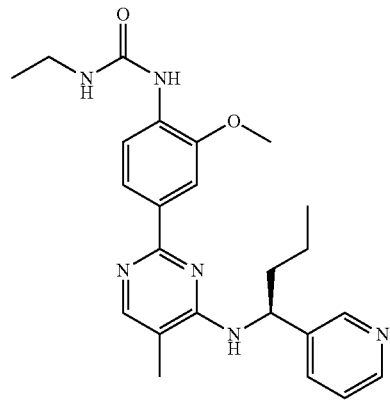
CYT997 (Cytopia)
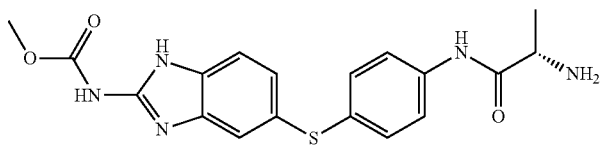
MN-029 (Denibulin.
MediciNova Angiogene)
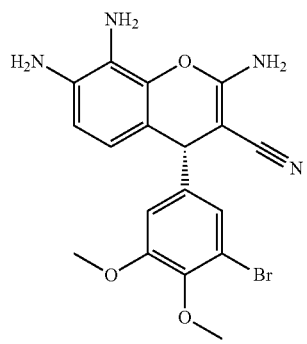
EPC2407 (EpiCept)
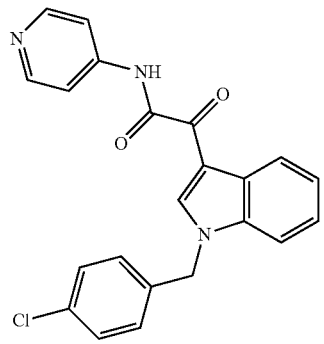
ZIO-301 (Indibulin, Ziopharm Oncology)

TABLE 1-continued
Examples of TPI structures
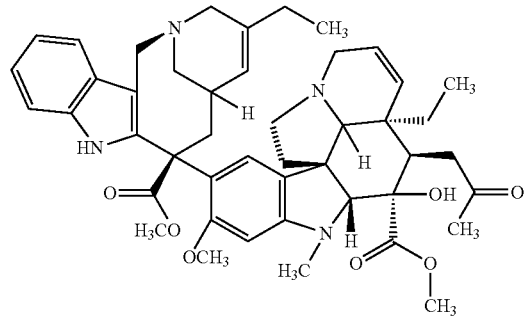
Vinorelbine
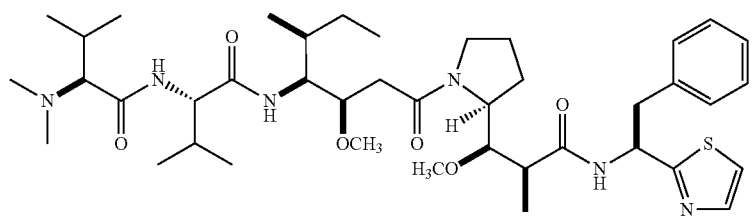
Dolastatin 10 (NCl)
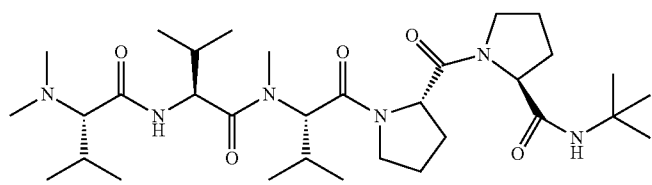
Tasidotin (synthadotin. Genzyme)
H—Cl
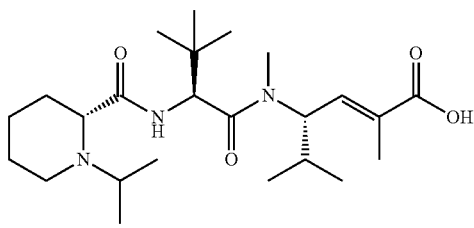
E7974 (Eisai)
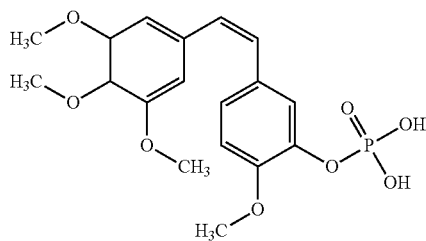
CA4 (Zybrestat™, OXiGENE)

TABLE 1-continued
Examples of TPI structures
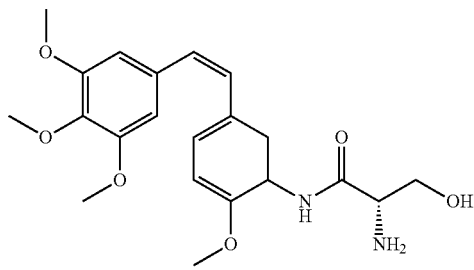
AVE8062 (AC7700, Sanofi Aventis)
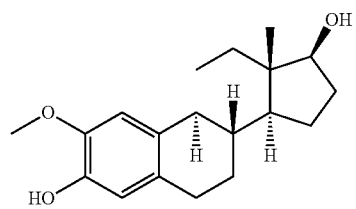
2-methoxyestradiol (2ME2 or Panzem®, EntreMed)
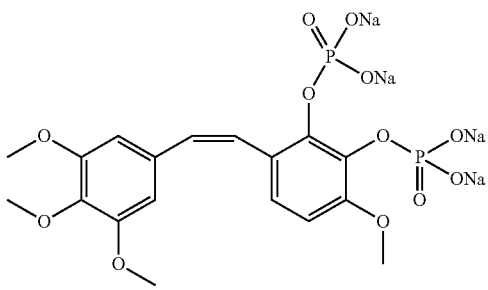
Oxi4503 (OXiGENE)
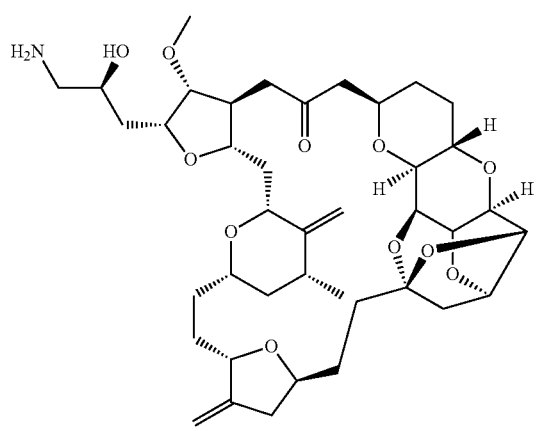
Eribulin Mesylate (E7389, Eisai)

In an embodiment the TPI is selected from a compound of formula (I) or salts, solvates or prodrugs thereof

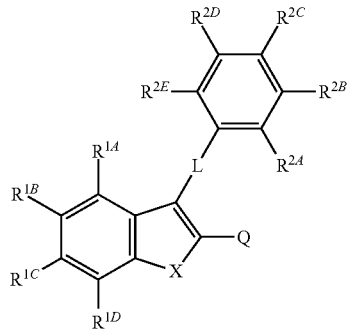

(I)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR"NR'", where each R'" independently represents H, optionally substituted alkyl, optionally substituted alkenyl, optionally substituted alkynyl, optionally substituted aryl and optionally substituted heteroaryl.

In some embodiments X is selected from
O,
S,
SO,
$SO_2$,
Se,
SeO,
$SeO_2$ or
NR where R is selected from
H,
O,
optionally substituted acyl selected from H—C(O)—, $C_1$-$C_{10}$ alkyl-C(O)— (preferably $C_1$-$C_6$ alkyl, more preferably $C_1$-$C_3$ alkyl), $C_4$-$C_8$ cycloalkyl-C(O)—, $C_6$-$C_{14}$ aryl-C(O)—, heteroaryl-C(O)— having from 2 to 10 carbon atoms and 1 to 4 heteroatoms selected from oxygen, nitrogen, selenium, and sulfur (including oxides of sulfur, selenium and nitrogen) within the ring or heterocyclyl-C(O)— having from 1 to 8 carbon atoms and from 1 to 4 heteroatoms selected from nitrogen, sulfur, oxygen, selenium or phosphorous within the ring. Examples of suitable acyl groups include formyl acetyl, propionyl, benzoyl (optionally substituted with methyl, methoxy, halogen, nitro, trifluoromethyl or cyano);

optionally substituted monovalent $C_2$-$C_{10}$ alkenyl group which may be straight chained or branched (preferably $C_2$-$C_6$ alkenyl) having at least 1 or from 1-2 carbon to carbon double bonds. Examples of suitable optionally substituted alkenyl groups include, ethenyl, n-propenyl, iso-propenyl, but-2-enyl, 1-propenyl, vinyl, nitrovinyl, cyano vinyl, or trifluorovinyl and styryl (optionally substituted with methyl, methoxy, halogen, nitro, trifluoromethane or cyano);

optionally substituted $C_1$-$C_{10}$ alkyl (preferably $C_1$-$C_6$ alkyl, more preferably $C_1$-$C_3$ alkyl). Examples of suitable alkyl groups include methyl, ethyl, n-propyl, iso-propyl, n-butyl, iso-butyl, n-hexyl, 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;

optionally substituted $C_6$-$C_{14}$ aryl;

optionally substituted $C_4$-$C_8$ cycloalkenyl;

optionally substituted $C_3$-$C_8$ cycloalkyl;

optionally substituted heteroaryl having from 2 to 10 carbon atoms and 1 to 4 heteroatoms selected from oxygen, nitrogen, selenium, and sulfur (including oxides of sulfur, selenium and nitrogen) within the ring;

optionally substituted heterocyclyl having from 1 to 8 carbon atoms and from 1 to 4 heteroatoms selected from nitrogen, sulfur, oxygen, selenium or phosphorous within the ring; and optionally substituted sulfonyl selected from H—S(O)$_2$—, $C_1$-$C_{10}$ alkyl-S(O)$_2$-(preferably $C_1$-$C_6$ alkyl, more preferably $C_1$-$C_3$ alkyl), $C_3$-$C_8$ cycloalkyl-S(O)$_2$—, $C_6$-$C_{14}$ aryl-S(O)$_2$—, heteroaryl-S(O)$_2$— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)$_2$— where the heterocyclyl group has from 1 to 8 carbon atoms and from 1 to 4 heteroatoms selected from nitrogen, sulfur, oxygen, selenium or phosphorous within the ring. Examples of sulfonyl groups include methylsulfonyl, ethylsulfonyl, benzenesulfonyl (optionally substituted with methyl, methoxy, halogen, nitro, trifluoromethane or cyano), methoxycarbo, trifluoromethane;

In some embodiments $R^{1A}$-$R^{1B}$ and $R^{2A}$-$R^{2E}$ are independently selected from the following groups:

$C_1$-$C_{10}$ alkyl, preferably $C_1$-$C_6$ alkyl, more preferably $C_1$-$C_3$ alkyl. Examples of suitable alkyl groups include methyl, ethyl, n-propyl, iso-propyl, n-butyl, iso-butyl and n-hexyl;

substituted $C_1$-$C_{10}$ alkyl group, preferably $C_1$-$C_6$ alkyl, more preferably $C_1$-$C_3$ alkyl. Examples of substituted alkyl groups include 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;

optionally subtituted acyl group selected from H—C(O)—, $C_1$-$C_{10}$ alkyl-C(O)—(preferably $C_1$-$C_6$ alkyl, more preferably $C_1$-$C_3$ alkyl), $C_3$-$C_8$ cycloalkyl-C(O)—, $C_6$-$C_{14}$ aryl-C(O)—, heteroaryl-C(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring) and heterocyclyl-C(O)— where the heterocyclyl group has from 1 to 8 carbon atoms and from 1 to 4 heteroatoms selected from nitrogen, sulfur, oxygen, selenium or phosphorous within the ring). Examples of acyl groups include formyl acetyl, propionyl, benzoyl (optionally substituted with methyl, methoxy, halogen, nitro, trifluoromethyl or cyano);

optionally substituted $C_1$-$C_{10}$ alkoxy group, preferably $C_1$-$C_6$ alkoxy, more preferably $C_1$-$C_3$ alkoxy. Examples of suitable alkoxy groups include methoxy, ethoxy, n-propoxy, iso-propoxy, n-butoxy, tert-butoxy, sec-butoxy, n-pentoxy, n-hexoxy and 1,2-dimethylbutoxy;

optionally substituted oxyacyl group selected from HOC(O)—, $C_1$-$C_{10}$ alkyl-OC(O)—(preferably preferably $C_1$-$C_6$ alkyl, more preferably $C_1$-$C_3$ alkyl), $C_3$-$C_8$ cycloalkyl-OC(O)—, $C_6$-$C_{14}$ aryl-OC(O)—, heteroaryl-OC(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-OC(O)— where the heterocyclyl group has from 1 to 8 carbon atoms and from 1 to 4 heteroatoms selected from nitrogen, sulfur, oxygen, selenium or phosphorous within the ring. Examples of oxyacyl groups include methoxycarbonyl, ethoxycarbonyl, propoxycarbonyl, butyloxycarbonyl, isobutyloxycarbonyl;

optionally substituted acyloxy group selected from —OC(O)—($C_1$-$C_{10}$ alkyl) (preferably $C_1$-$C_6$ alkyl, more preferably $C_1$-$C_3$ alkyl), —OC(O)—($C_6$-$C_{14}$ aryl), —C(O)O-heteroaryl where the heteroaryl group has from 2 to 10 carbon atoms and 1 to 4 heteroatoms selected from oxygen, nitrogen, selenium, and sulfur (including oxides of sulfur, selenium and nitrogen) within the ring, and —C(O)O-heterocyclyl where the heterocyclyl group has from 1 to 8 carbon atoms and from 1 to 4 heteroatoms selected from nitrogen, sulfur, oxygen, selenium or phosphorous within the ring. Examples of acyloxy groups include acetoxy and propioxy;

optionally substituted ($C_6$-$C_{14}$ aryl)-($C_1$-$C_{10}$ alkyl) group. Preferably the aryl group is $C_6$-$C_{10}$ aryl. Preferably the alkyl group is $C_1$-$C_6$ alkyl, more preferably $C_1$-$C_3$ alkyl. Examples of substituted arylalkyl groups include benzyl, phenethyl, 1-hydroxybenzyl, and 1-thiobenzyl;

optionally substituted sulfinyl group selected from H-S(O)—, $C_1$-$C_{10}$ alkyl-S(O)—(preferably $C_1$-$C_6$ alkyl, more preferably $C_1$-$C_3$ alkyl), $C_3$-$C_8$ cycloalkyl-S(O)—, $C_6$-$C_{14}$ aryl-S(O)— (preferably, the aryl group has from 6 to 14 carbon atoms), heteroaryl-S(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)— where the heterocyclyl group has from 1 to 8 carbon atoms and from 1 to 4 heteroatoms selected from nitrogen, sulfur, oxygen, selenium or phosphorous within the ring. Examples of sulfinyl groups include methylsulfinyl, ethylsulfinyl, benzene sulfinyl (optionally substituted with methyl, methoxy, halogen, nitro, trifluoromethane or cyano), methoxysulfinyl, ethoxysulfinyl;

optionally substituted sulfonyl group selected from H—S(O)$_2$—, $C_1$-$C_{10}$ alkyl-S(O)$_2$— (preferably $C_1$-$C_6$ alkyl, more preferably $C_1$-$C_3$ alkyl), $C_3$-$C_8$ cycloalkyl-S(O)$_2$—, $C_6$-$C_{14}$ aryl-S(O)$_2$—, heteroaryl-S(O)$_2$— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)$_2$— where the heterocyclyl group has from 1 to 8 carbon atoms and from 1 to 4 heteroatoms selected from nitrogen, sulfur, oxygen, selenium or phosphorous within the ring. Examples of sulfonyl groups include methylsulfonyl, ethylsulfonyl, benzenesulfonyl (optionally substituted with methyl, methoxy, halogen, nitro, trifluoromethane or cyano), methoxycarbo, trifluoromethane;

optionally substituted oxyacylamino group of the formula —NR*C(O)OR* where each R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of oxyacylamino groups include methoxycarbonylamido, and ethoxycarbonyl amido;

optionally substituted oxythioacyl group selected from HO—C(S)—, $C_1$-$C_{10}$ alkylO—C(S)— (preferably $C_1$-$C_6$ alkyl, more preferably $C_1$-$C_3$ alkyl), $C_3$-$C_8$ cycloalkylO—C (S)—, $C_6$-$C_{14}$ arylO—C(S)—, heteroarylO—C(S)— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclylO—C(S)— where the heterocyclyl group has from 1 to 8 carbon atoms and from 1 to 4 heteroatoms selected from nitrogen, sulfur, oxygen, selenium or phosphorous within the ring. Examples of oxythioacyl groups include methoxythiocarbonyl and ethoxythiocarbonyl;

optionally substituted thioacyloxy group selected from H—C(S)—O—, $C_1$-$C_{10}$ alkyl-C(S)—O— (preferably $C_1$-$C_6$ alkyl, more preferably $C_1$-$C_3$ alkyl), $C_3$-$C_8$ cycloalkyl-C (S)—O—, $C_6$-$C_{14}$ aryl-C(S)—O—, heteroaryl-C(S)—O— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-C(S)—O— where the heterocyclyl group has from 1 to 8 carbon atoms and from 1 to 4 heteroatoms selected from nitrogen, sulfur, oxygen, selenium or phosphorous within the ring. Examples of thioacyloxy groups include thionoacetoxy and thionopropionoxy;

optionally substituted sulfinylamino group selected from H—S(O)—NR*—, $C_1$-$C_{10}$ alkyl-S(O)—NR*— (preferably the alkyl groups are $C_1$-$C_6$ alkyl, more preferably $C_1$-$C_3$ alkyl), $C_3$-$C_8$ cycloalkyl-S(O)—NR*—, $C_6$-$C_{14}$ aryl-S(O)—NR*—, heteroaryl-S(O)—NR*— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)—NR*— where the heterocyclyl group has from 1 to 8 carbon atoms and from 1 to 4 heteroatoms selected from nitrogen, sulfur, oxygen, selenium or phosphorous within the ring. R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of sulfinylamino groups include methylsulfinylamino, ethylsulfinylamino, and benzenesulfinylamino (optionally substituted with methyl, methoxy, halogen, nitro, trifluoromethane or cyano);

amino group;

substituted amino groupsof the formula —NR*R* where each R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of substituted amino groups include residues of L-valine, D-valine, L-alanine, D-alanine, aspartic acid, and alanylserine, N-methylamino, and N,N'-dimethylamino;

optionally substituted sulfonylamino group selected from H—S(O)$_2$—NR*—, $C_1$-$C_{10}$alkyl-S(O)$_2$—NR*— (preferably $C_1$-$C_6$ alkyl, more preferably $C_1$-$C_3$ alkyl), $C_3$-$C_8$ cycloalkyl-S(O)$_2$— NR*—, $C_6$-$C_{14}$ aryl-S(O)$_2$—NR*—, heteroaryl-S(O)$_2$—NR*— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)2—NR*— where the heterocyclyl group has from 1 to 8 carbon atoms and from 1 to 4 heteroatoms selected from nitrogen, sulfur, oxygen, selenium or phosphorous within the ring. R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of sulfonylamino groups include methylsulfonylamino, ethylsulfonylamino and benzene sulfonylamino (optionally substituted with methyl, methoxy, halogen, nitro, trifluoromethane or cyano);

optionally substituted oxysulfinylamino group selected from HO—S(O)—NR*—, $C_1$-$C_{10}$ alkylO—S(O)—NR*— (preferably $C_1$-$C_6$ alkyl, more preferably $C_1$-$C_3$ alkyl), $C_3$-$C_8$ cycloalkylO—S(O)—NR*—, $C_6$-$C_{14}$ arylO—S(O)—NR*—, heteroarylO—S(O)—NR*— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclylO—S(O)—NR*— where the heterocyclyl group has from 1 to 8 carbon atoms and from 1 to 4 heteroatoms selected from nitrogen, sulfur, oxygen, selenium or phosphorous within the ring. R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of suitable oxysulfinylamino groups include methoxysulfinylamino and ethoxysulfinylamino;

optionally substituted oxysulfonylamino group selected from HO—S(O)$_2$—NR*—, $C_1$-$C_{10}$ alkylO—S(O)$_2$—NR*— (preferably $C_1$-$C_6$ alkyl, more preferably $C_1$-$C_3$ alkyl), $C_3$-$C_8$ cycloalkylO—S(O)$_2$—NR*—, $C_6$-$C_{14}$ arylO—S(O)$_2$—NR*—, heteroarylO—S(O)$_2$—NR*— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclylO—S(O)$_2$—NR*— where the heterocyclyl group has from 1 to 8 carbon atoms and from 1 to 4 heteroatoms selected from nitrogen, sulfur, oxygen, selenium or phosphorous within the ring. R* is independently hydrogen, C$_1$-C$_{10}$ alkyl (preferably C$_1$-C$_6$ alkyl, more preferably C$_1$-C$_3$ alkyl), C$_3$-C$_8$ cycloalkyl, C$_6$-C$_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring. Examples of oxysulfonylamino groups include methoxysulfonylamino and ethoxysulfonylamino;

optionally substituted C$_2$-C$_{10}$ alkenyl group which may be straight chained or branched and have at least 1 or from 1-2 carbon to carbon double bonds. Preferably optionally substituted C$_2$-C$_6$ alkenyl. Examples of suitable optionally substituted alkenyl groups include ethenyl, n-propenyl, isopropenyl, but-2-enyl, 1-propenyl, vinyl, nitrovinyl, cyano vinyl, or trifluorovinyl and styryl (optionally substituted with methyl, methoxy, halogen, nitro, trifluoromethane or cyano);

optionally substituted C$_2$-C$_{10}$ alkynyl group having at least 1 or from 1-2 carbon to carbon triple bonds. Preferably C$_2$-C$_6$ alkynyl. Examples of suitable alkynyl groups include 1-propynyl, ethynyl, propargyl, pent-2-ynyl and trimethylsilylethynyl.

In some embodiments L is selected from the following groups:
C=O,
O,
S,
SO,
SO$_2$,
Se,
SeO,
SeO$_2$,
C=NZ' where Z' is H, optionally substituted C$_1$-C$_{10}$ alkyl (preferably C$_1$-C$_6$, more preferably C$_1$-C$_3$), optionally substituted C$_6$-C$_{14}$ aryl or optionally substituted amino, or
NR' where R' is selected from
H,
O,
optionally substituted acyl group selected from H—C(O)—, C$_1$-C$_{10}$ alkyl-C(O)— (preferably C$_1$-C$_6$ alkyl, more preferably C$_1$-C$_3$ alkyl), C$_3$-C$_8$ cycloalkyl-C(O)—, C$_6$-C$_{14}$ aryl-C(O)—, heteroaryl-C(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring and heterocyclyl-C(O)— where the heterocyclyl group has from 1 to 8 carbon atoms and from 1 to 4 heteroatoms selected from nitrogen, sulfur, oxygen, selenium or phosphorous within the ring). Examples of acyl groups include formyl acetyl, propionyl, benzoyl (optionally substituted with methyl, methoxy, halogen, nitro, trifluoromethyl or cyano);

optionally substituted C$_2$-C$_{10}$ alkenyl group which may be straight chained or branched and have at least 1 or from 1-2 carbon to carbon double bonds. Preferably optionally substituted C$_2$-C$_6$ alkenyl. Examples of suitable optionally substituted alkenyl groups include ethenyl, n-propenyl, isopropenyl, but-2-enyl, 1-propenyl, vinyl, nitrovinyl, cyano vinyl, or trifluorovinyl and styryl (optionally substituted with methyl, methoxy, halogen, nitro, trifluoromethane or cyano);

optionally substituted C$_1$-C$_{10}$ alkyl, preferably C$_1$-C$_6$ alkyl, more preferably C$_1$-C$_3$ alkyl. Examples of suitable alkyl groups include methyl, ethyl, 1-hydroxyethyl, 1-thioethyl, methoxyiminomethyl, ethoxyiminomethyl, 1-(hydroxyimino)ethyl, 1-(hydroxyimino)propyl, 1-hydrazinoethyl, 1-hydrazinopropyl, hydroxyiminomethyl, 2-oxopropyl, 2-oxobutyl, 3-oxobutyl, 3-oxopentyl, nitromethyl, 1-nitromethyl, and 2-nitroethyl;

optionally substituted C$_6$-C$_{14}$ aryl;
optionally substituted C$_4$-C$_8$ cycloalkenyl;
optionally substituted C$_3$-C$_8$ cycloalkyl;
optionally substituted heteroaryl having from 2 to 10 carbon atoms and 1 to 4 heteroatoms selected from oxygen, nitrogen, selenium, and sulfur (including oxides of sulfur, selenium and nitrogen) within the ring optionally substituted heterocyclyl having from 1 to 8 carbon atoms and from 1 to 4 heteroatoms selected from nitrogen, sulfur, oxygen, selenium or phosphorous within the ring; or optionally substituted sulfonyl selected from H—S(O)$_2$—, C$_1$-C$_{10}$ alkyl-S(O)$_2$— (preferably C$_1$-C$_6$ alkyl, more preferably C$_1$-C$_3$ alkyl), C$_3$-C$_8$ cycloalkyl-S(O)$_2$—, C$_6$-C$_{14}$ aryl-S(O)$_2$—, heteroaryl-S(O)$_2$— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-S(O)$_2$— where the heterocyclyl group has from 1 to 8 carbon atoms and from 1 to 4 heteroatoms selected from nitrogen, sulfur, oxygen, selenium or phosphorous within the ring. Examples of sulfonyl groups include methylsulfonyl, ethylsulfonyl, benzenesulfonyl (optionally substituted with methyl, methoxy, halogen, nitro, trifluoromethane or cyano), methoxycarbo, trifluoromethane;

In some embodiments Q is selected from the following groups:
H;
CN;
halogen, preferably Br or Cl;
trialkylsilyl, in which each alkyl group is independently C$_1$-C$_{10}$ alkyl (preferably C$_1$-C$_6$ alkyl, more preferably C$_1$-C$_3$ alkyl);

optionally substituted C$_1$-C$_{10}$ alkyl (preferably C$_1$-C$_6$ alkyl, more preferably C$_1$-C$_3$ alkyl). Examples of suitable alkyl groups include methyl, ethyl, propyl, butyl, aminoalkyl, oxyacylaminoalkyl and oxysulphonylaminoalkyl;

optionally substituted C$_2$-C$_{10}$ alkenyl group which may be straight chained or branched and have at least 1 or from 1-2 carbon to carbon double bonds. Preferably optionally substituted C$_2$-C$_6$ alkenyl. Examples of suitable optionally substituted alkenyl groups include ethenyl, n-propenyl, isopropenyl, but-2-enyl, 1-propenyl, vinyl, nitrovinyl, cyano vinyl, or trifluorovinyl and styryl (optionally substituted with methyl, methoxy, halogen, nitro, trifluoromethane or cyano);

optionally substituted C$_2$-C$_{10}$ alkynyl group having at least 1 or from 1-2 carbon to carbon triple bonds. Preferably C$_2$-C$_6$ alkynyl. Examples of suitable alkynyl groups include 1-propynyl, ethynyl, propargyl, pent-2-ynyl, trimethylsilylethynyl and 2-alkylethynyl.

optionally substituted oxyacyl selected from HOC(O)—, C$_1$-C$_{10}$ alkyl-OC(O)— (preferably preferably C$_1$-C$_6$ alkyl, more preferably C$_1$-C$_3$ alkyl), C$_3$-C$_8$ cycloalkyl-OC(O)—, $C_6$-$C_{14}$ aryl-OC(O)—, heteroaryl-OC(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring, and heterocyclyl-OC(O)— where the heterocyclyl group has from 1 to 8 carbon atoms and from 1 to 4 heteroatoms selected from nitrogen, sulfur, oxygen, selenium or phosphorous within the ring. Examples of oxyacyl groups include methoxycarbonyl, ethoxycarbonyl, propoxycarbonyl, butyloxycarbonyl, isobutyloxycarbonyl;

optionally substituted acyl group selected from H—C(O)—, $C_1$-$C_{10}$ alkyl-C(O)— (preferably $C_1$-$C_6$ alkyl, more preferably $C_1$-$C_3$ alkyl), $C_3$-$C_8$ cycloalkyl-C(O)—, $C_6$-$C_{14}$ aryl-C(O)—, heteroaryl-C(O)— where the heteroaryl group has from 2 to 10 carbon atoms and 1 to 4 heteroatoms selected from oxygen, nitrogen, selenium, and sulfur (including oxides of sulfur, selenium and nitrogen) within the ring and heterocyclyl-C(O)— where the heterocyclyl group has from 1 to 8 carbon atoms and from 1 to 4 heteroatoms selected from nitrogen, sulfur, oxygen, selenium or phosphorous within the ring). Examples of acyl groups include formyl acetyl, propionyl, benzoyl (optionally substituted with methyl, methoxy, halogen, nitro, trifluoromethyl or cyano);

optionally substituted acylamino of the formula —NR*C(O)R* where each R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring;

optionally substituted aminoacylamino, of the formula —NR*C(O)NR*R* where each R* is independently hydrogen, $C_1$-$C_{10}$ alkyl (preferably $C_1$-$C_6$ alkyl, more preferably $C_1$-$C_3$ alkyl), $C_3$-$C_8$ cycloalkyl, $C_6$-$C_{14}$ aryl, heteroaryl having from 2 to 10 carbon atoms and 1 to 4 heteroatoms selected from oxygen, nitrogen, selenium, and sulfur (including oxides of sulfur, selenium and nitrogen) within the ring and heterocyclyl having from 1 to 8 carbon atoms and from 1 to 4 heteroatoms selected from nitrogen, sulfur, oxygen, selenium or phosphorous within the ring;

OR″, where R″ is selected from H or an optionally substituted $C_1$-$C_{10}$ alkyl (preferably $C_1$-$C_6$ alkyl, more preferably $C_1$-$C_3$ alkyl). Examples of suitable OR″ groups include hydroxy, methoxy, ethoxy, n-propoxy, iso-propoxy, n-butoxy, tert-butoxy, sec-butoxy, n-pentoxy, n-hexoxy and 1,2-dimethylbutoxy;

NR″R″, preferably R″ is selected from H, heteroaryl having from 2 to 10 carbon atoms and 1 to 4 heteroatoms selected from oxygen, nitrogen, selenium, and sulfur (including oxides of sulfur, selenium and nitrogen) within the ring, amino, amino$C_1$-$C_{10}$ alkyl (preferably $C_1$-$C_6$ alkyl, more preferably $C_1$-$C_3$ alkyl), hydroxyl, hydroxy$C_1$-$C_{10}$ alkyl (preferably $C_1$-$C_6$ alkyl, more preferably $C_1$-$C_3$ alkyl), $C_1$-$C_{10}$ alkoxy (preferably $C_1$-$C_6$ alkoxy, more preferably $C_1$-$C_3$ alkoxy), $C_1$-$C_{10}$alkoxy $C_1$-$C_{10}$alkyl, oxyacyl, oxyacylalkyl, oxyacylamino, oxyacylaminoalkyl, guanidine, guanidinoalkyl or an optionally substituted $C_1$-$C_{10}$ alkyl group (preferably $C_1$-$C_6$ alkyl, more preferably $C_1$-$C_3$ alkyl). Examples of suitable NR″R″ groups include $NH_2$, alkylamino, dialkylamino, heteroarylamino, aminoalkylamino, hydroxyalkylamino, alkoxyalkylamino, oxyacylalkylamino, oxyacylaminoalkylamino, guanidinoalkylamino;

SR, preferably R″ is selected from H, heteroaryl having from 2 to 10 carbon atoms and 1 to 4 heteroatoms selected from oxygen, nitrogen, selenium, and sulfur (including oxides of sulfur, selenium and nitrogen) within the ring, amino, amino$C_1$-$C_{10}$ alkyl (preferably $C_1$-$C_6$ alkyl, more preferably $C_1$-$C_3$ alkyl), hydroxyl, hydroxy$C_1$-$C_{10}$ alkyl (preferably $C_1$-$C_6$ alkyl, more preferably $C_1$-$C_3$ alkyl), $C_1$-$C_{10}$ alkoxy (preferably $C_1$-$C_6$ alkoxy, more preferably $C_1$-$C_3$ alkoxy), $C_1$-$C_{10}$alkoxy $C_1$-$C_{10}$alkyl, oxyacyl, oxyacylalkyl, oxyacylamino, oxyacylaminoalkyl, guanidine, guanidinoalkyl or an optionally substituted $C_1$-$C_{10}$ alkyl group (preferably $C_1$-$C_6$ alkyl, more preferably $C_1$-$C_3$ alkyl). Examples of suitable S′R″ groups include alkylthio, aminoalkylthio, heteroarylthio, aminoalkylthio, hydroxyalkylthio, alkoxyalkylthio, oxyacylalkylthio, oxyacylaminoalkylthio, guanidinoalkylthio;

hydrazine.

In the definitions of the groups X, $R^{1A}$-$R^{1B}$, Q, L and $R^{2A}$-$R^{2E}$, the term "optionally substituted" refers to a group which may or may not be further substituted or fused (so as to form a condensed polycyclic group) with one or more groups selected from hydroxy, acyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, heterocyclyloxy, oxyacyl, oxime, oxime ether, hydrazone, —$NHC(NH)NH_2$, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono-and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like.

In one embodiment $R^{2D}$, $R^{2C}$, and $R^{2B}$ are methoxy and L is a carbonyl group (C=O).

Accordingly, in this embodiment the TPIs are represented by formula (Ia) or salts, solvates, or prodrugs thereof

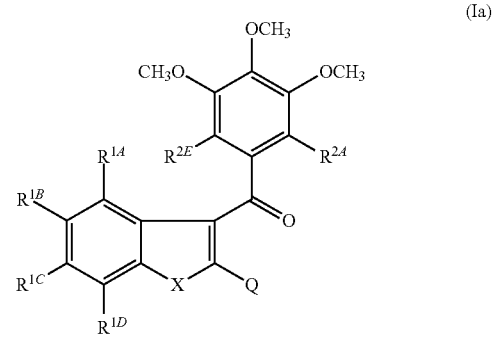

(Ia)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

$R^{2A}$ and $R^{2E}$ independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted acyl and optionally substituted oxyacyl, or NR"'NR"', where each R"' independently represents H, optionally substituted alkyl, optionally substituted alkenyl, optionally substituted alkynyl, optionally substituted aryl and optionally substituted heteroaryl.

In another embodiment, $R^{1A}$, $R^{1B}$, $R^{2A}$ and $R^{2E}$ represent H and $R^{1C}$, $R^{2B}$, $R^{2C}$ and $R^{2D}$ represents $C_{1-3}$ alkoxy.

Accordingly, in this embodiment the TPI is represented by formula (Ib) or salts, solvates or prodrugs thereof

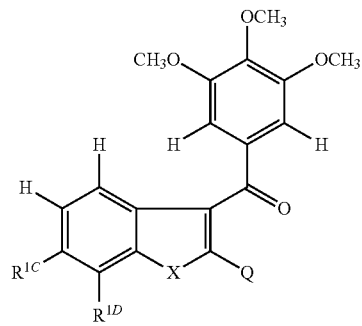

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1C}$ represents $C_{1-3}$ alkoxy;

$R^{1D}$ represents hydroxy or amino;

Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted acyl and optionally substituted oxyacyl, or NR"'NR"', where each R"' independently represents H, optionally substituted alkyl, optionally substituted alkenyl, optionally substituted alkynyl, optionally substituted aryl and optionally substituted heteroaryl.

In a preferred embodiment $R^{1C}$ represents methoxy.

For the compounds represented by formulae I, Ia and Ib, X is preferably selected from O, S and NR. More preferably X is O or NR and most preferably X is O.

Accordingly, in another embodiment the TPI is represented by formula II:

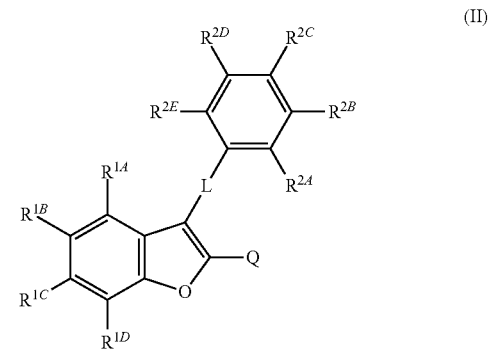

wherein;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

In this embodiment it is preferred that L is a carbonyl group (C=O). Also, preferably at least one of $R^{2D}$, $R^{2C}$ or $R^{2B}$ represents a hydroxy or $C_{1-3}$ alkoxy group. More preferably when X=O, L is a carbonyl group an $R^{2D}$, $R^{2C}$ and $R^{2B}$ represent methoxy. Even more preferably when X=O, L is a carbonyl group, $R^{2D}$, $R^{2C}$, and $R^{2B}$ represent methoxy and $R^{1A}$, $R^{1B}$, $R^{2A}$, R2E are H.

Furthermore, for the compounds of formula (I), (Ia), (Ib) and (II) it is preferred that Q represents H, CN, optionally substituted $C_{2-4}$ alkynyl, optionally substituted $C_{2-6}$ alkenyl, optionally substituted $C_{1-4}$ alkyl, hydroxy, optionally substituted oxyacyl, NR"R", SR" (where each R" is independently H, optionally substituted $C_{1-4}$alkyl, optionally substituted heterocyclyl, optionally substituted heteroaryl), NR"NR''' (where each R''' is independently H, $C_{1-3}$ alkyl), optionally substituted acylamino, or halogen.

In some embodiments Q is independently selected from the following groups:

H;

CN;

halogen, preferably Br or Cl;

alkyl group, preferably methyl, ethyl, propyl, butyl;

substituted alkyl group, preferably amino, oxyacylaminoalkyl and oxysulphonylaminoalkyl;

optionally substituted alkenyl, preferably ethenyl, 2-alkylethenyl, 2-oxyacylethenyl, 2-aminoacylethenyl;

optionally substituted alkynyl, preferably ethynyl, 2-alkylethynyl;

optionally substituted oxyacyl;

OR", preferably hydroxy, methoxy, ethoxy;

NR"R", preferably $NH_2$, alkylamino, dialkylamino, heteroarylamino, aminoalkylamino, hydroxyalkylamino, alkoxyalkylamino, oxyacylalkylamino, oxyacylaminoalkylamino, guanidinoalkylamino;

SR", preferably alkylthio, aminoalkylthio, heteroarylthio, aminoalkylthio, hydroxyalkylthio, alkoxyalkylthio, oxyacylalkylthio, oxyacylaminoalkylthio, guanidinoalkylthio; hydrazine.

In a further preferred embodiment the TPI is a compound of formula (III) or a salt, solvate or prodrug thereof

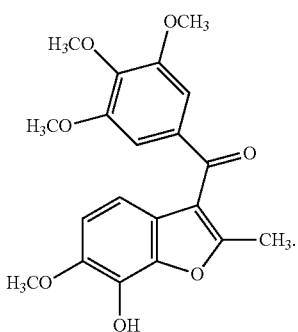 [SMILES: COc1cc(C(=O)c2c(C)oc3c(O)c(OC)ccc23)cc(OC)c1OC]

The compound of formula (III) (2-Methyl-7-hydroxy-3-(3,4,5-trimethoxybenzoyl)-6-methoxybenzofuran) can be prepared by the synthetic methodology described in PCT/AU2007/000101 (WO 07/087684).

The compounds of formula I, Ia, Ib, II or III have been observed to be potent tubulin polymerisation inhibitors (TPIs). An important aspect of the compounds of formulae I, Ia, Ib, II and III is the combination of the specific C-6 and C-7 substituents together with the C-2 Q-group (especially C-2 methyl) which appears to confer greater potency and selectivity when compared to other structurally related TPI compounds. In these compounds selectivity is not simply reliant on the predisposition of tumour vasculature towards collapse when challenged with the VDA but on a capacity of the VDA to distinguish between tumour endothelial cells and normal endothelial cells. Normal endothelial cells, found in healthy tissues, are in a "quiescent" state and tumour endothelial cells are in an "activated" state. Most VDAs do not distinguish between these two states, for example, Combretastatin A4 (CA4) is equally potent against quiescent and activated endothelial cells. However, the compounds of formulae I, Ia, Ib, II and particularly III show selectivity towards tumor endothelial cells (activated) over normal endothelial cells (quiescent).

In some embodiments, the TPI for use in the present method is a compound of formula I, Ia, Ib or II or a salt, solvate or prodrug thereof wherein $R^{1C}$ is $C_{1-3}$ alkoxy, $R^{1D}$ is hydroxyl and Q is optionally substituted $C_{1-10}$ (or $C_{1-6}$ or $C_{1-3}$) alkyl.

The TPI compounds of formula I, Ia, Ib, II or III may be prepared by known methods including those disclosed in U.S. Patent Application Publication No. U.S. 2005/0130221 A1 and U.S. Patent Application Publication No. U.S. 2010/0004208 A1 which are incorporated herein by reference.

It will be appreciated that the TPIs and compounds of formula I, Ia, Ib, II, or III can be administered to a subject as a pharmaceutically acceptable salt thereof. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts eg sodium or potassium salts, or alkyl esters (eg methyl, ethyl) of the phosphate group.

It will also be appreciated that any compound that is a prodrug of a TPI or a compound of formula I, Ia, Ib, II, and III are also within the scope and spirit of the invention. The term "pro-drug" is used in its broadest sense and encompasses those derivatives that are converted in vivo to a compound (for instance, a compound of formulae I, Ia, Ib, II, and III). Such derivatives would readily occur to those skilled in the art, and include, for example, compounds where the free hydroxy group (for instance at C-7 position or $R^{1D}$) is converted into an ester, such as an acetate or phosphate ester, or where a free amino group (for instance at C-7 position or $R^{1D}$) is converted into an amide (e.g., α-amino acid amide). Procedures for esterifying, e.g. acylating, the compounds are well known in the art and may include treatment of the compound with an appropriate carboxylic acid, anhydride or chloride in the presence of a suitable catalyst or base. A particularly preferred prodrug is a disodium phosphate ester. The disodium phosphate ester (in particular a C-7 disodium phosphate ester of a compound of formula III) of the compound may be useful in increasing the solubility of the compounds. This would, for instance, may allow for delivery of the compound in a benign vehicle like saline. The disodium phosphate ester may be prepared in accordance with the methodology described in Pettit, G. R., et al, Anticancer Drug Des., 1995, 10, 299. Other texts which generally describe prodrugs (and the preparation thereof) include: Design of Prodrugs, 1985, H. Bundgaard (Elsevier); The Practice of Medicinal Chemistry, 1996, Camille G. Wermuth et al., Chapter 31 (Academic Press); and A Textbook of Drug Design and Development, 1991, Bundgaard et al., Chapter 5, (Harwood Academic Publishers).

In some embodiments, the TPI for use in the present method is a compound of formula (IV)

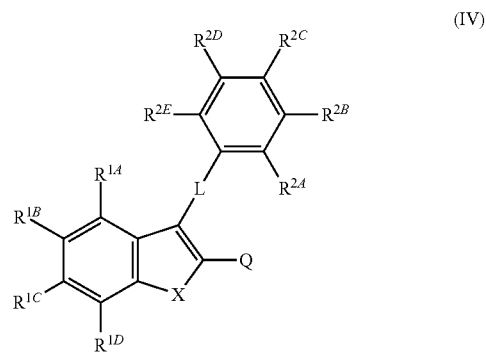

(IV)

wherein, X, $R^{1A}$-$R^{1C}$ and $R^{2A}$-$R^{2E}$, L and Q are as defined in formula I, Ia, Ib, II or III, and $R^{1D}$ is $OR^3$ or $NHR^3$, and $R^3$ is H or an ester. When $R^3$ is an ester, the ester may consist of a carbonyl adjacent to an ether linkage (such as an acetate ester), or may be an inorganic ester (such as a phosphate, sulfate, nitrate or borate ester). In some embodiments, the ester is an acetate or a phosphate ester. A particularly preferred ester is a disodium phosphate ester.

The compounds of formulae I, Ia, Ib, II, and III (or a salt or prodrug thereof) may be in crystalline form either as the free compound or as a solvate (e.g. hydrate) and it is intended that both forms are within the scope of the present invention. Methods of solvation are generally known within the art.

Chemical Definitions

"Alkyl" refers to monovalent alkyl groups which may be straight chained or branched and preferably have from 1 to 10 carbon atoms or more preferably 1 to 6 carbon atoms, and even more preferably 1 to 3 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms, and even more preferably 1 to 3 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like.

"Aryl" refers to an unsaturated aromatic carbocyclic group having a single ring (eg., phenyl) or multiple condensed rings (eg., naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to —alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tent-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH═CH$_2$), n-propenyl (—CH$_2$CH═CH$_2$), iso-propenyl (—C(CH$_3$)═CH$_2$), but-2— enyl (—CH$_2$CH═CHCH$_3$), and the like.

"Alkenyloxy" refers to the group alkenyl-O— wherein the alkenyl group is as described above.

"Alkenylene" refers to divalent alkenyl groups preferably having from 2 to 8 carbon atoms and more preferably 2 to 6 carbon atoms. Examples include ethenylene (-CH═CH-), and the propenylene isomers (e.g., —CH$_2$CH═CH— and —C(CH$_3$)═CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$C≡CCH$_2$—CH$_3$), and the like.

"Alkynyloxy" refers to the group alkynyl-O— wherein the alkynyl groups is as described above.

"Alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Aminoacylamino" refers to the group —NR*C(O) NR*R* where each R* is independently hydrogen, alkyl, cycloalkyl, aryl, heteroaryl, and heterocyclyl and where each of alkyl, cycloalkyl, aryl, heteroaryl and heterocyclyl is as described herein.

"Acylamino" refers to the group —NR*C(O)R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR*-alkyl, —OC(O)NR*-aryl, —OC(O)NR*-heteroaryl, and —OC(O)NR*-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR*C(O)O-alkyl, —NR*C(O)O-aryl, —NR*C(O)O-heteroaryl, and NR*C(O)O-heterocyclyl where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR*)—R* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR*)—OR* where each R* is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 8 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, and the like.

"Cycloalkenyl" refers to cyclic alkenyl groups having a single cyclic ring and at least one point of internal unsaturation, preferably incorporating 4 to 8 carbon atoms. Examples of suitable cycloalkenyl groups include, for instance, cyclobut-2-enyl, cyclopent-3-enyl, cyclohex-4-enyl, cyclooct-3-enyl and the like.

"Halo" or "halogen" refers to fluoro, chloro, bromo and iodo.

"Heteroaryl" refers to a monovalent aromatic heterocyclic group which fulfils the Hückel criteria for aromaticity (ie. contains 4n+2π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg., pyridyl, pyrrolyl or N-oxides thereof or furyl) or multiple condensed rings (eg., indolizinyl, benzoimidazolyl, coumarinyl, quinolinyl, isoquinolinyl or benzothienyl).

"Heterocyclyl" refers to a monovalent saturated or unsaturated group having a single ring or multiple condensed rings, preferably from 1 to 8 carbon atoms and from 1 to 4 heteroatoms selected from nitrogen, sulfur, oxygen, selenium or phosphorous within the ring. The most preferred heteroatom is nitrogen.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR*—P(O)(R)(OR*) where R* represents H, alkyl, cycloalkyl, alkenyl, or aryl, R represents OR* or is hydroxy or amino and R*** is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR*—, alkyl-S(O)—NR*—, cycloalkyl-S(O)—NR*—, aryl-S(O)—NR*—, heteroaryl-S(O)—NR*—, and heterocyclyl-S(O)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR*—, alkyl-S(O)$_2$—NR*—, cycloalkyl-S(O)$_2$—NR*—, aryl-S(O)$_2$—NR*—, heteroaryl-S(O)$_2$—NR*—, and heterocyclyl-S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR*—, alkylO—S(O)—NR*—, cycloalkylO—S(O)—NR*—, arylO—S(O)—NR*—, heteroarylO—S(O)—NR*—, and heterocyclylO—S(O)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR*—, alkylO—S(O)$_2$—NR*—, cycloalkylO—S(O)$_2$—NR*—, arylO—S(O)$_2$—NR*—, heteroarylO—S(O)$_2$—NR*—, and heterocyclylO—S(O)$_2$—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R*R*N—C(S)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR*—, alkyl-C(S)—NR*—, cycloalkyl-C(S)—NR*—, aryl-C(S)—NR*—, heteroaryl-C(S)—NR*—, and heterocyclyl-C(S)—NR*—, where R* is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R*R*N—S(O)—, where each R* is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R*R*N—S(O)$_2$—, where each R* is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxy, acyl, alkyl, alkoxy, alkenyl, alkenyloxy, alkynyl, alkynyloxy, amino, aminoacyl, thio, arylalkyl, arylalkoxy, aryl, aryloxy, acylamino, cyano, halogen, nitro, sulfo, phosphono, phosphorylamino, phosphinyl, heteroaryl, heteroaryloxy, heterocyclyl, heterocyclyloxy, oxyacyl, oxime, oxime ether, hydrazone, —NHC(NH)NH$_2$, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono-and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like. An optionally substituted amino group may also include amino acid and peptide residues.

Dosing and Administration

As understood in the art, the terms "combination therapy", "combination treatment", or "pharmaceutical combination" refer to the use of more than one medication or other therapy (vs. monotherapy, which is any therapy taken alone), to treat a single disease. A "Pharmaceutical combination" therapy, for example, may be achieved by prescribing/administering separate drugs, or, where available, dosage forms that contain more than one active ingredient (such as fixed-dose combinations).

The methods and uses of the present invention encompass the administration of the mTOR inhibitor or a salt, solvate or prodrug thereof (combination partner a) and vascular disrupting agent or a salt, solvate or prodrug thereof (combination partner b) to a single patient, and is intended to include treatment regimens in which the agents are not necessarily administered by the same route of administration or at the same time. Accordingly, combination partners (a) and (b) may be administered together, one after the other or separately in one combined unit dosage form or in two separate unit dosage forms. The unit dosage form may also be a fixed combination such as a pharmaceutical composition which comprises both partner (a) (or a salt, solvate or prodrug thereof) and partner (b) (or a salt, solvate or prodrug thereof).

In particular, a therapeutically effective amount of each of the combination partner of the combination of the invention may be administered simultaneously or sequentially and in any order, and the components may be administered separately or as a fixed combination.

For example, the method of the invention may comprise: (i) administration of partner (a) in free or pharmaceutically acceptable salt form; and (ii) administration of partner (b) in free or pharmaceutically acceptable salt form, simultaneously or sequentially in any order, in jointly therapeutically effective amounts, preferably in synergistically effective amounts, e.g., in daily or intermittent dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that converts in vivo to the combination partner as such.

As such it will be appreciated that the combination partners may be presented as a "kit of parts" for use in the treatment of renal cancer. The kit may comprise a package where the combination partners are supplied separately for co-administration with instructions for use in the particular therapy.

The effective dosage of each of the combination partners employed in the combination of the invention may vary depending on the particular compound or pharmaceutical composition employed, the mode of administration, and the severity/grade of the renal cancer being treated.

Daily dosages for combination partners (a) and (b) will, of course, vary depending on a variety of factors, e.g., the compound chosen, the particular condition to be treated and the desired effect. In general, however, satisfactory results are achieved on administration of agent (a) at daily dosage rates of about 0.05 to 20 mg/kg per day, particularly 1 to 20 mg/kg per day, e.g. 0.4 to 16 mg/kg per day, as a single dose or in divided doses. Combination partner (a) and partner (b) may be administered by any conventional route, in particular enterally, e.g., orally, e.g., in the form of tablets, capsules, drink solutions or parenterally, e.g., in the form of injectable solutions or suspensions. Suitable unit dosage forms for oral administration comprise from about 0.02 to 50 mg active ingredient, usually 0.1 to 30 mg and 2 to 25 mg, 4 to 20 mg e.g. combination partner (a) or (b), together with one or more pharmaceutically acceptable diluents or carriers therefore.

Combination partner (b) may be administered to a human in a daily dosage range of 0.5 to 1000 mg. Suitable unit dosage forms for oral administration comprise from about 0.1 to 500 mg active ingredient, together with one or more pharmaceutically acceptable diluents or carriers therefore. Methods and administration regimes for delivery known mTOR inhibitors would be known to the skilled clinician.

For instance, an administration regime may include adding the TPI (e.g., compound of formula I, Ia, Ib, II, or III) at an assigned dose level by I.V. on days 1 and 8 (of a 21 day cycle) where the mTOR inhibitor is given as an oral daily dose (e.g., 10 mg/day). In this embodiment the compound of formula (III) may be dosed at a level of between 4 to 16 mg/kg.

Thus, while the skilled person will readily be able to determine suitable doses of the mTOR inhibitor and the vascular disrupting agent, in one embodiment, everolimus is administered at a dosage of about 5 to about 15 mg. In yet another embodiment, everolimus is administered at a dosage of about 10 mg.

In another embodiment, BNC105P is administered at a dosage of about 8 mg/m$^2$ to about 16 mg/m$^2$. In one particular embodiment, BNC105P is administered at a dosage of 16 mg/m$^2$.

Additional Therapies

The methods of the present invention may utilise the combination of an mTOR inhibitor and a vascular disrupting agent in conjunction with other therapeutic agents and treatment modalities such as tumor irradiation. For example, the combination therapy of the present invention may be used in conjunction with another chemotherapeutic, antibody and or immunotherapeutic that is suitable for administration to a patient for the treatment of renal cancer.

Examples of therapeutic agents that may be administered in conjunction with the combination of an mTOR inhibitor and a vascular disrupting agent include tyrosine kinase inhibitors, such as VEGF-directed tyrosine kinase inhibitors and proteasome inhibitors. By way of example, tyrosine kinase inhibitors include sunitinib (Sutent), sorafenib (Nexavar), axitinib (Inlyta) and pazopanib (Votrient). Another therapeutic agent used in the treatment of renal cancer is carfilzomib (Kyprolis), a selective proteasome inhibitor. By way of non-limiting examples, immunotherapeutic agents useful in the invention include interleukin 2 (IL2), and interferon alpha (IFNα). One non-limiting example of a suitable therapeutic antibody that may be used is bevacizumab (Avastin).

EXAMPLES

Example 1

Disruptor -1 Trial: Study of BNC105P in Combination with Everolimus for Metastatic Clear Cell Renal Cell Carcinoma The objective of the study was to determine the response rate of patients administered BNC105P (vascular disrupting agent) in combination with everolimus (mTOR inhibitor) in patients who had progressed from prior tyrosine kinase inhibitor therapy. In addition, the present inventors determined the improvement in 6-months progression free survival (PFS) with the addition of BNC105P to everolimus (Afinitor). A control group of patients received everolimus alone.

The medical histories of patients were obtained prior to commencement of the study. Patients selected for the study exhibited a Karnofsky Performance Score of ≥70, had metastatic or locally advanced inoperable renal cell carcinoma, had progressive disease after 1-2 prior treatments with VEGF-directed tyrosine kinase inhibitors, had no active brain metastases, and good bone marrow, liver and kidney function.

Patients in the BNC105P in combination with everolimus study group (the "combination arm") were administered 10 mg oral everolimus daily. On days 1 and 8 of the 21 day cycle period, the patients were administered 16 mg/m$^2$ BNC105P, which had been determined to be the maximum tolerated dose, by intravenous infusion over a 10 minute period (FIG. 1). Treatment was continued until disease progressed, intolerable toxicity became apparent, or until consent was withdrawn. A control group of patients were administered with everolimus alone.

All patients in the study were followed for disease progression and survival. Prior to commencing treatment, patients enrolled in the study were subject to disease assessment including: CT of chest, abdomen and pelvis; CT of the head or brain MRI; bone scan; echocardiography (ECHO) or multiple gated acquisition scan (MUGA). At every 3 cycles of treatment, CT scans of chest, abdomen and pelvis, and bone scans were performed to determine disease progression.

Example 2

Disease Evaluation and Response Criteria

The criteria for disease evaluation included:

Measurable disease: —the presence of at least one measurable lesion. If the measurable disease is restricted to a solitary lesion, its neoplastic nature should be confirmed by cytology/histology.

Measurable lesions: —lesions that can be accurately measured in at least one dimension with longest diameter (LD) >20 mm using conventional techniques or >10 mm with spiral CT scan.

Non-measurable lesions—all other lesions, including small lesions (longest diameter <20 mm with conventional techniques or <10 mm with spiral CT scan), i.e., bone lesions, leptomeningeal disease, ascites, pleural/pericardial effusion, inflammatory breast disease, lymphangitis cutis/pulmonis, cystic lesions, and also abdominal masses that are not confirmed and followed by imaging techniques.

Baseline documentation of "target" and "non-target" lesions-all measurable lesions up to a maximum of five lesions per organ and 10 lesions in total, representative of all involved organs should be identified as target lesions and recorded and measured at baseline. Target lesions should be selected on the basis of their LD. The baseline sum LD will be used as reference by which to characterize the objective tumor. All other lesions (or sites of disease) should be identified as non-target lesions and should also be recorded at baseline. Measurements of these lesions are not required, but the presence or absence of each should be noted throughout follow-up.

The response criteria for the evaluation of target lesions were as follows:

Complete Response (CR): Disappearance of all target lesions

Partial Response (PR): At least a 30% decrease in the sum of the LD of target lesions, taking as reference the baseline sum LD Progressive Disease (PD): At least a 20% increase in the sum of the LD of target lesions, taking as reference the smallest sum LD recorded since the treatment started or the appearance of one or more new lesions Stable Disease (SD): Neither sufficient shrinkage to qualify for PR nor sufficient increase to qualify for PD, taking as reference the smallest sum LD since the treatment started The response criteria for the evaluation of non-target lesions were as follows:

Complete Response (CR) Disappearance of all non-target lesions and normalization of tumor marker level Incomplete Response/Stable Disease (SD): Persistence of one or more non-target lesion(s) or/and maintenance of tumor marker level above the normal limits Progressive Disease (PD): Appearance of one or more new lesions and/or unequivocal progression of existing non-target lesions Time to disease progression was determined as a measurement from the start of the treatment until the criteria for disease progression is met (or death occurs), taking as reference the smallest measurements recorded since the treatment started. The time to progression, in patients with documented disease progression at their first disease evaluation, were considered the time between initiation of therapy and the date of first documentation of disease progression.

Example 3

Statistical Analysis

All safety analyses were performed using the Intent-To-Treat (ITT) population. The standard summary statistics for continuous variables were: mean, standard deviation, median, quartiles, maximum and minimum. The standard summary statistics for discrete values were: count and proportion. Progression free survival (PFS) was defined as date on study to date of disease progression or death, and overall survival of patients was summarized by Kaplan-Meier methods performed among the ITT population.

The 6-month PFS and response rates among evaluable patients were summarized by proportions together with 95% confidence intervals. Counts and proportions by toxicity were presented with exact binomial 95% confidence intervals for the following (ITT population).

In addition, Chi-square or Fisher's Exact test were used to correlate biomarkers with responders and non-responders. Multivariate logistic regression was further used to model response rates after adjusting for different patient characteristics. Multivariate Cox regression was used to model time to event outcomes after adjusting for different patient characteristics.

Example 4

Progression Free Survival in Patient Subpopulations

Figure 2:
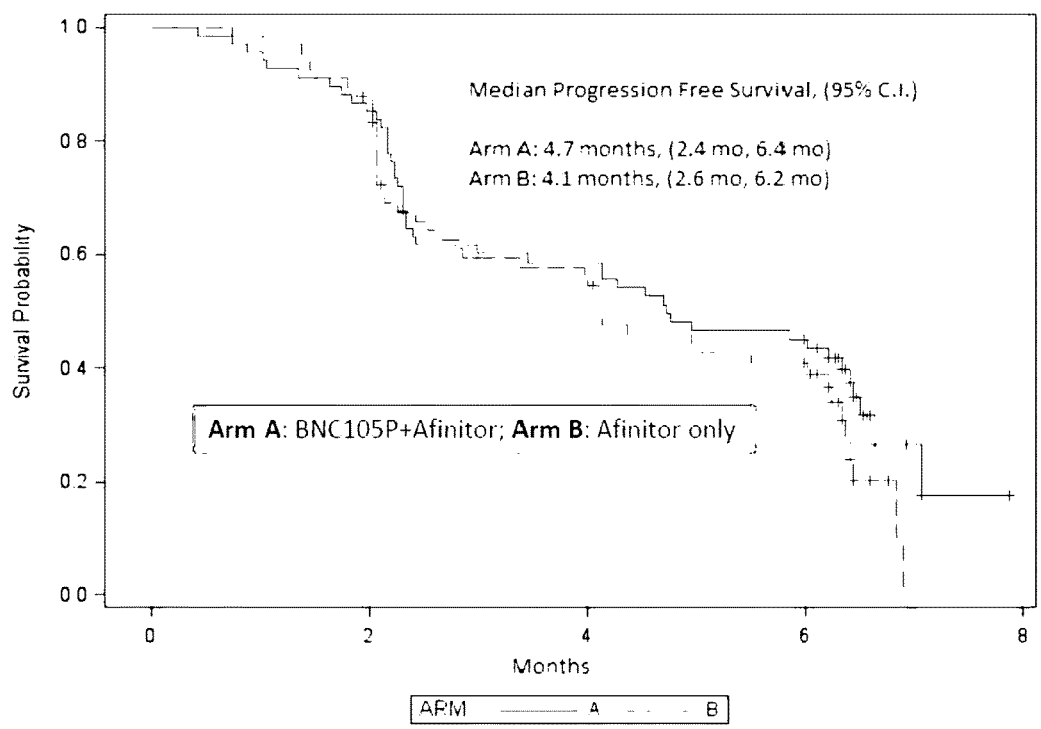
FIG. 2. Median Progression Free Survival for all patients (Arm A: BNC105P+Afinitor; Arm B (control): Afinitor only).

The present inventors analysed the results of the study and determined that a similar proportion of patients were free of disease progression at 6 months in both the group administered BNC105P in combination with everolimus (23 patients), and in the control group administered with everolimus alone (20 patients; FIG. 2).

Figure 3:
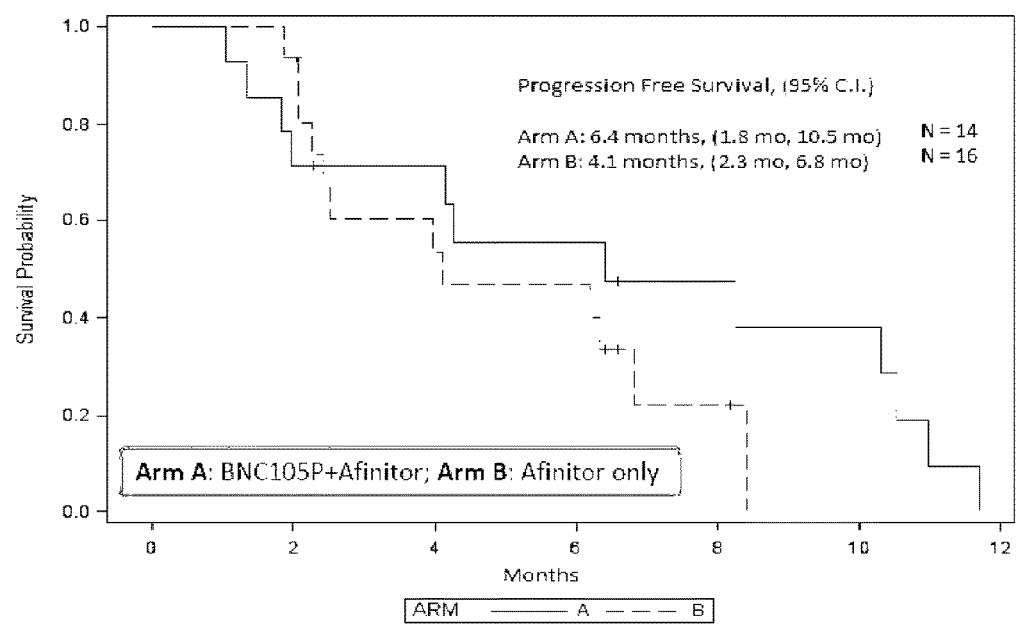
FIG. 3. Progression Free Survival data for Fuhrman Grade II patients.
Figure 4:
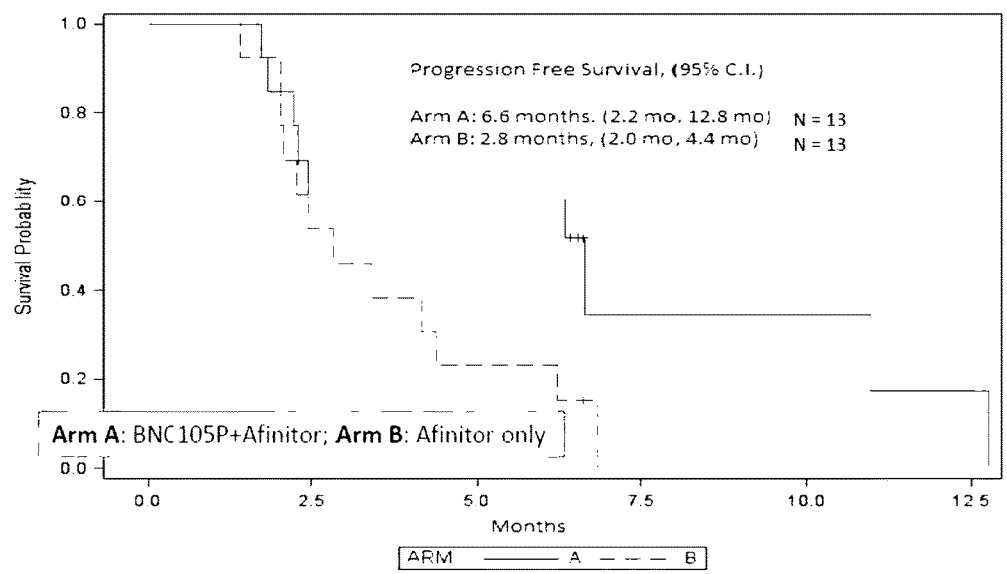
FIG. 4. Progression Free Survival data for patients with liver metastases.
Figure 5:
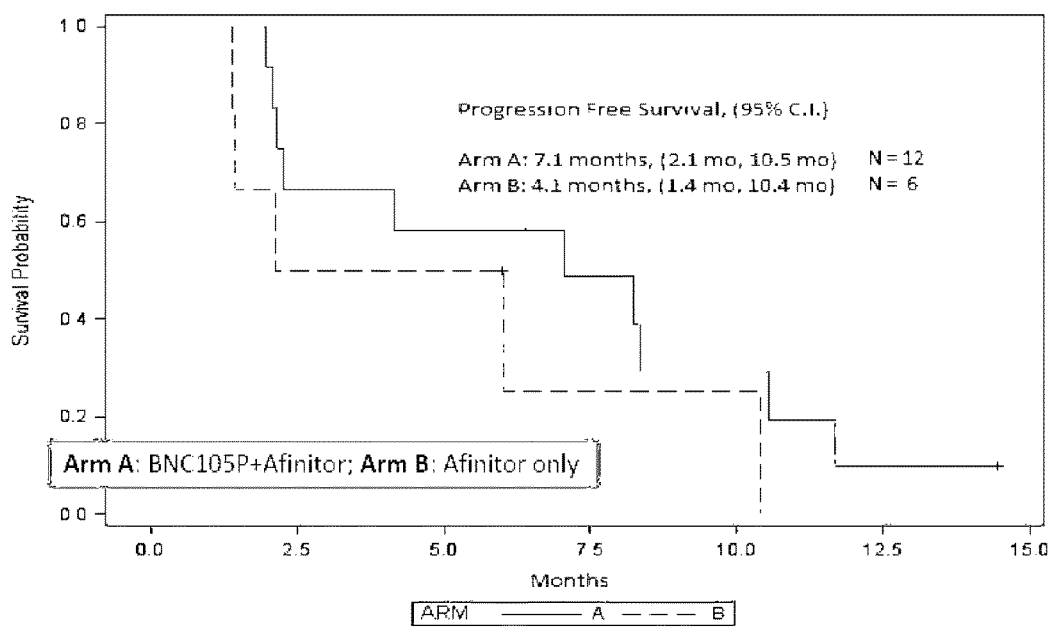
FIG. 5. Progression Free Survival data for patients with prior nephrectomy.

Patient subgroup analysis, however, demonstrated that certain biomarkers were predictive for an increase in progression free survival. In this regard, patients having a Fuhrman Grade 2 tumor prior to commencement of treatment with BNC105P and everolimus experienced a 2.3 month increase in progression free survival compared to patients treated with everolimus (Afinitor) alone (FIG. 3). Patients having liver metastases prior to commencement of treatment with BNC105P and everolimus experienced a 3.8 month increase in progression free survival compared to treatment with everolimus alone (FIG. 4). In addition, patients having a nephrectomy prior to commencement of treatment with BNC105P and everolimus experienced a 3 month increase in progression free survival compared to patients treated with everolimus alone (FIG. 5).

Thus, the present inventors identified three biomarkers (Fuhrman Grade 2 tumor; liver metastases; and prior nephrectomy) that are predictive for response to treatment with a combination of an mTOR inhibitor and a vascular disrupting agent, compared to patients treated with an mTOR inhibitor alone.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

The present application claims priority from AU 2014902535, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Fuhrman et al. (1982) Am J Surg Pathol, 6(7):655-653
Maroto and Rini (2014) Clin Cancer Res, 20(8):1-12
Vasudev et al. (2012) BMC Medicine, 10:112

The invention claimed is:

1. A method of treating renal cancer in a patient in need of said treatment, the method comprising identifying a patient having a Fuhrman tumor grade of 2 or greater, the presence of liver metastases, and/or a prior nephrectomy, administering an mTOR inhibitor and a vascular disrupting agent to the patient, and administering at least one further therapeutic agent and/or tumor irradiation to the patient.

2. The method of claim 1, wherein the vascular disrupting agent is a tubulin polymerisation inhibitor.

3. The method of claim 2, wherein the tubulin polymerisation inhibitor is a compound of formula (I) or a salt, solvate or prodrug thereof

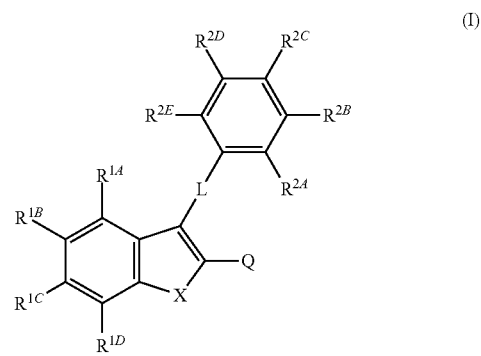

(I)

wherein;

X represents O, S, SO, $SO_2$, Se, SeO, $SeO_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, SO$_2$, Se, SeO, SeO$_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'''NR''', where each R''' independently represents H, optionally substituted alkyl, optionally substituted alkenyl, optionally substituted alkynyl, optionally substituted aryl and optionally substituted heteroaryl.

4. The method of claim 2, wherein the tubulin polymerisation inhibitor is a compound of formula (Ia) or a salt, solvate or prodrug thereof

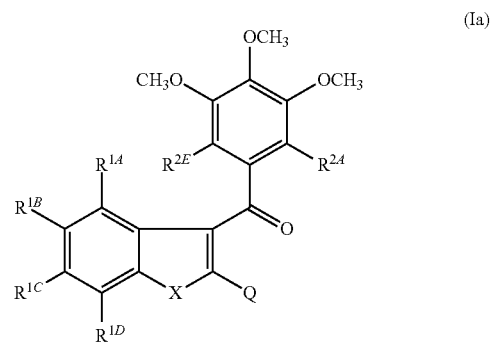

(Ia)

wherein;

X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

$R^{2A}$ and $R^{2E}$ independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted heterocyclyl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

5. The method of claim 2, wherein the tubulin polymerisation inhibitor is a compound of formula (Ib) or a salt, solvate or prodrug thereof

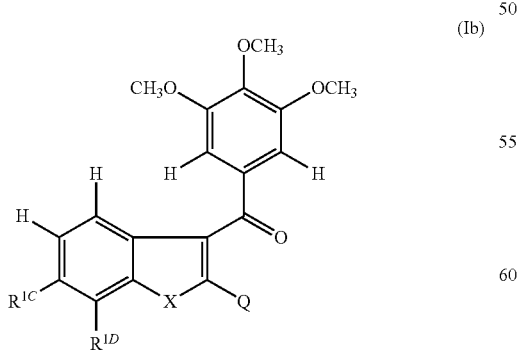

wherein;
X represents O, S, SO, SO$_2$, Se, SeO, SeO$_2$ or NR where R is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, and optionally substituted sulfonyl;

$R^{1C}$ represents $C_{1-3}$ alkoxy;

$R^{1D}$ represents hydroxy or amino;

Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted aryl, optionally substituted heteroaryl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

6. The method of claim 2, wherein the tubulin polymerisation inhibitor is a compound of formula (II) or a salt, solvate or prodrug thereof

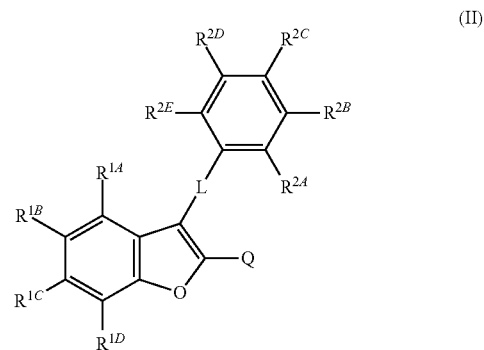

wherein;
$R^{1A}$ and $R^{1B}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or $R^{1A}$ and $R^{1B}$ together form an optionally substituted aryl, optionally substituted heterocyclyl, optionally substituted heteroaryl, optionally substituted cycloalkyl, or optionally substituted cycloalkenyl;

$R^{1C}$ represents $C_{1-3}$ alkoxy, $C_{1-3}$ alkylthio, $C_{1-3}$ alkylamino, or $C_{1-3}$ dialkylamino;

$R^{1D}$ represents hydroxy or amino;

L represents C=O, O, S, SO, $SO_2$, Se, SeO, $SeO_2$, C=NZ', or NR' where Z' is H, optionally substituted alkyl, optionally substituted aryl or optionally substituted amino; and where R' is selected from H, O, optionally substituted acyl, optionally substituted alkenyl, optionally substituted alkyl, optionally substituted aryl, optionally substituted cycloalkenyl, optionally substituted cycloalkyl, optionally substituted heteroaryl, optionally substituted heterocyclyl, or optionally substituted sulfonyl;

$R^{2A}$-$R^{2E}$ each independently represents H, carboxy, cyano, dihalomethoxy, halogen, hydroxy, nitro, pentahaloethyl, phosphorylamino, phosphono, phosphinyl, sulfo, trihaloethenyl, trihalomethanethio, trihalomethoxy, trihalomethyl, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacylimino, optionally substituted oxyacyloxy, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, optionally substituted thioacylamino, or optionally substituted thioacyloxy; or any of $R^{2A}$ and $R^{2B}$, $R^{2B}$ and $R^{2C}$, $R^{2C}$ and $R^{2D}$, and $R^{2D}$ and $R^{2E}$, together form an optionally substituted aryl, optionally substituted heterocyclyl, optionally substituted heteroaryl, optionally substituted cycloalkyl, or optionally substituted cycloalkenyl; and Q represents H, CN, halogen, trialkylsilyl, optionally substituted alkyl, optionally substituted alkenyl, optionally substituted alkynyl, optionally substituted acyl, optionally substituted oxyacyl, optionally substituted acylamino, optionally substituted aminoacylamino, OR", SR" or NR"R", where each R" independently represents, H, optionally substituted alkyl, optionally substituted alkenyl, optionally substituted alkynyl, optionally substituted heterocyclyl, optionally substituted aryl, optionally substituted heteroaryl, optionally substituted acyl and optionally substituted oxyacyl, or NR'"NR'", where each R'" independently represents H, optionally substituted alkyl, optionally substituted alkenyl, optionally substituted alkynyl, optionally substituted aryl and optionally substituted heteroaryl.

7. The method of claim 2, wherein the tubulin polymerisation inhibitor is a compound of formula (III) or a salt, solvate or prodrug thereof

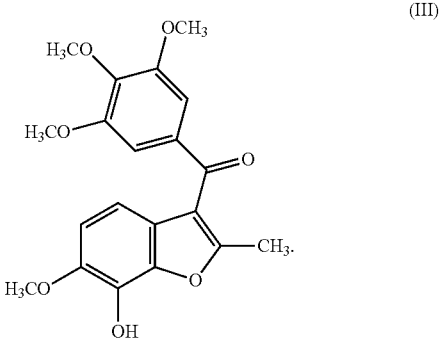 [SMILES: COc1cc(C(=O)c2c(C)oc3c(O)c(OC)ccc23)cc(OC)c1OC]

8. The method of claim 2, wherein the tubulin polymerisation inhibitor is selected from 2-methyl-7-hydroxy-3-(3,4,5-trimethoxybenzoyl)-6-methoxybenzofuran and disodium [6-methoxy-2-methyl-3-(3,4,5-trimethoxybenzoyl)-1-benzofuran-7-yl] phosphate.

9. The method of claim 1, wherein the mTOR inhibitor is selected from BEZ235, deforolimus, PI-103, rapamycin, temsirolimus, everolimus, ABT 578, SAR 543 and AP 23841.

10. The method of claim 9, wherein the tubulin polymerisation inhibitor is disodium [6-methoxy-2-methyl-3-(3,4,5-trimethoxybenzoyl)-1-benzofuran-7-yl] phosphate and the mTOR inhibitor is everolimus.

11. The method of claim 1, wherein the mTOR inhibitor and the vascular disrupting agent are administered separately.

12. The method of claim 11, wherein the patient is administered the mTOR inhibitor and then subsequently administered the vascular disrupting agent.

13. The method of claim 1, wherein the mTOR inhibitor and the vascular disruption agent are administered as a combination formulation.

14. The method of claim 1, wherein the at least one further therapeutic agent is selected from a chemotherapeutic, an antibody, an immunotherapeutic, and combinations thereof.

* * * * *